US 9,700,640 B2
Jul. 11, 2017

(12) United States Patent
Wheatley et al.

(54) STABILIZED ULTRASOUND CONTRAST AGENT

(75) Inventors: Margaret A. Wheatley, Media, PA (US); Boriphat Methachan, Lampang (TH); Carl D. Solis, Paoli, PA (US)

(73) Assignee: Drexel University, Philadelphia, PA (US)

( * ) Notice: Subject to any disclaimer, the term of this patent is extended or adjusted under 35 U.S.C. 154(b) by 1435 days.

(21) Appl. No.: 13/497,019

(22) PCT Filed: Sep. 20, 2010

(86) PCT No.: PCT/US2010/049518
§ 371 (c)(1),
(2), (4) Date: Jun. 5, 2012

(87) PCT Pub. No.: WO2011/035254
PCT Pub. Date: Mar. 24, 2011

(65) Prior Publication Data
US 2012/0237450 A1   Sep. 20, 2012

Related U.S. Application Data

(60) Provisional application No. 61/244,355, filed on Sep. 21, 2009, provisional application No. 61/355,454, filed on Jun. 16, 2010.

(51) Int. Cl.
*A61K 49/22* (2006.01)

(52) U.S. Cl.
CPC .................................. *A61K 49/223* (2013.01)

(58) Field of Classification Search
CPC .................................................. A61K 49/223
See application file for complete search history.

(56) References Cited

U.S. PATENT DOCUMENTS

| | | | |
|---|---|---|---|
| 5,352,436 A | 10/1994 | Wheatley et al. | |
| 6,139,819 A | 10/2000 | Unger et al. | |
| 6,217,850 B1 * | 4/2001 | Dugstad | A61K 49/223 424/9.52 |
| 6,221,337 B1 * | 4/2001 | Dugstad | A61K 49/22 424/9.52 |
| 2005/0025710 A1 | 2/2005 | Schneider et al. | |
| 2006/0222711 A1 | 10/2006 | Kipp et al. | |
| 2006/0257321 A1 * | 11/2006 | Schneider | A61K 49/223 424/9.52 |
| 2007/0081946 A1 | 4/2007 | Schneider et al. | |

FOREIGN PATENT DOCUMENTS

EP   0052575 A2   5/1982

OTHER PUBLICATIONS

Abdelwahed et al., "Investigation of nanocapsules stabilization by amorphous excipients during freeze-drying and storage." 2006, Euro. Pharm. Biopharm., 63:87-94.
Basude et al., "Generation of ultraharmonics in surfactant based ultrasound contrast agents: use and advantages." 2001, Ultrasonics, 39:437-44.
Basude et al., "Influence of environmental conditions on a new surfactant-based contrast agent: ST68." 2000, Ultrasound Med. Biol., 26:621-8.
Binks, "Particles as surfactants—similarities and differences" 2002, Curr Opin Colloid Interface Sci 7:21-41.
Bogdahn et al., 2001, "Transcranial color-coded duplex sonography (TCCS)." In: Dunitz, M. (Ed.) Ultrasound Contrast Agents: Basic principles and clinical applications, Martin Dunitz Ltd., London, UK pp. 253-265.
Bouakaz et al., "WFUMB Safety Symposium on Echo-Contrast Agents: nature and types of ultrasound contrast agents." 2007, Ultrasound Med Biol 33:187-96.
Crowe et al., "Stabilization of dry membranes by mixtures of hydroxyethyl starch and glucose: the role of vitrification." 1997, Cryobiol., 35:20-30.
Dickinson et al., "Factors controlling the formation and stability of air bubbles stabilized by partially hydrophobic silica nanoparticles." 2004, Langmuir 20:8517-8525.
Eisner et al., "Stability of foams containing proteins, fat particles and nonionic surfactants." 2007, Chem Eng Sci 62:1974-1987.
Forsberg et al., "Comparison of air and perfluorocarbon filled microbubbles for ultrasound contrast studies." 1996, IEEE Ultrasonics Symp., 2:1337-40.
Forsberg et al., "Effect of filling gases on the backscatter from contrast microbubbles: theory and in vivo measurements." 1999, Ultrasound in Med. and Biol. 25:1203-1211.
Gonzenbach et al., "Ultrastable particle-stabilized foams." 2006, Chem Int Ed 45:3526-3530.
Harris, "Solubilization—A micellar phenomenon." 1958, J Am Oil Chem Soc 35:428-435.
Hua et al., "Freeze-Drying of Liposomes with Cryoprotectants and Its Effect on Retention Rate of Encapsulated Ftorafur and Vitamin A." 2003, Drying Technol., 21(8):1491-505.
Huang et al., "Liposomes As Ultrasound Imaging Contrast Agents and As Ultrasound-Sensitive Drug Delivery Agents." 2002, Cell Molec. Biol. Letters, 7:233-5.
Hunter et al., "The role of particles in stabilising foams and emulsions." 2008, Adv Colloid Int Sci 137:57-81.
Jeong et al., "Effect of cryoprotectants on the reconstitution of surfactant-free nanoparticles of poly(DL-lactide-co-glycolide)." 2005, J Microencap 22:593-601.
Kaptay, "On the equation of the maximum capillary pressure induced by solid particles to stabilize emulsions and foams and on the emulsion stability diagrams." 2006, Colloids and Surfaces A: Physicochem Eng Aspects 282-283:387-401.
Oeffinger et al., "Development and characterization of a nano-scale contrast agent." 2004, Ultrasonic 42:343-347.
Ozer et al., "Influence of freezing and freeze-drying on the stability of liposomes dispersed in aqueous media" 1988, Acta Pharm. Technol., 34:129-39.

(Continued)

*Primary Examiner* — Michael G Hartley
*Assistant Examiner* — Leah Schlientz
(74) *Attorney, Agent, or Firm* — Saul Ewing LLP; Kathryn Doyle; Brian R. Landry

(57) ABSTRACT

Provided is a particle-stabilized ultrasound contrast agent (UCA) and methods of preparing same. Also provided is a method for preparing a lyoprotected UCA, a freeze-dried lyoprotected UCA, and a reconstituted freeze-dried lyoprotected UCA.

12 Claims, 25 Drawing Sheets

(56) References Cited

OTHER PUBLICATIONS

Simperler et al., "Glass transition temperature of glucose, sucrose, and trehalose: an experimental and in silico study." 2006, J Phys Chem B 110:19678-84.
Vignes-Adler et al., "New foams: Fresh challenges and opportunities." 2008, Current Opinion in Colloids & Interface Science 13:141-149.
Wang et al., "Langmuir Trough Study of Surfactant Mixtures Used in the Production of a New Ultrasound Contrast Agent Consisting of Stabilized Microbubbles." 1996, J. Phys. Chem., 100:13815-21.
Wheatley and Singhal, "Structural studies on stabilized microbubbles: development of a novel contrast agent for diagnostic ultrasound." 1995, Reactive Polymers 25:157-166.
Wheatley et al., "Surfactant-stabilized contrast agent on the nanoscale for diagnostic ultrasound imaging." 2006, Ultrasound Med. Biol., 32:83-93.
Yu et al., "Determination of the glass properties of D-mannitol using sorbitol as an impurity." 1998, J Pharm Sci 87:774-7.
International Search Report, International Application No. PCT/US2010/049518, Oct. 29, 2010.
Written Opinion of the International Searching Authority, International Application No. PCT/US2010/049518, Oct. 29, 2010.
Abdelwahed, W., et al., "Freeze-drying of nanoparticles: Formulation, process and storage considerations", Advanced Drug Delivery Reviews, vol. 58, 1688-1713 (2006).
Christensen, D., et al., "$\alpha,\alpha'$-trehalose 6,6'-dibehenate in non-phospholipid-based liposomes enables direct interaction with trehalose, offering stability during freeze-drying", Biochimica et Biophysica Acta, vol. 1778, 1365-1373 (2008).
Meister, E., et al., "Freeze-Dry Microscopy of Protein/Sugar Mixtures: Drying Behavior, Interpretation of Collapse Temperatures and a Comparison to Corresponding Glass Transition Data", Journal of Pharmaceutical Sciences, vol. 98, 3072-3087 (2009).
Wang, B., et al., "Impact of Sucrose level on Storage Stability of Proteins in Freeze-Dried Solids: I. Correlation of Protein-Sugar Interaction With Native Structure Preservation", Journal of Pharmaceutical Sciences, vol. 98, 3131-3144 (2009).

* cited by examiner

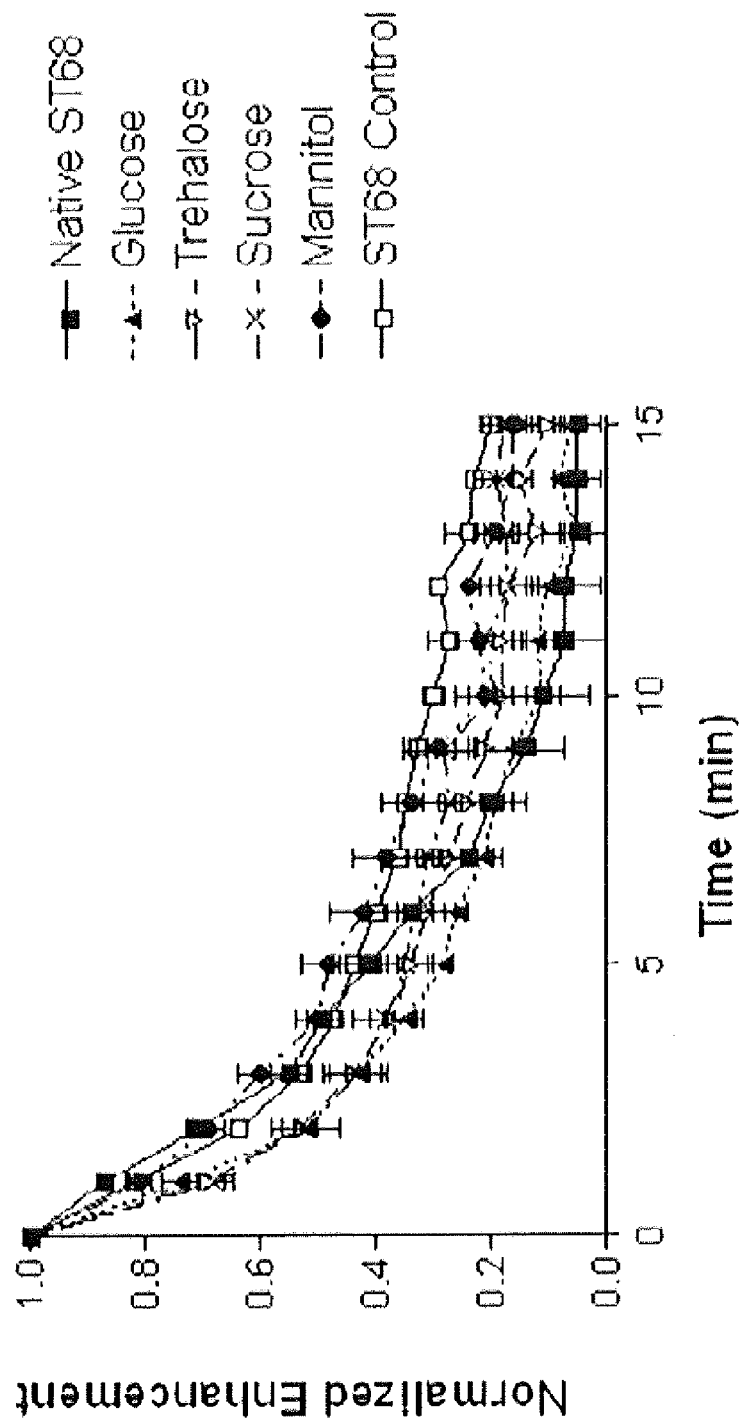

STABILIZED ULTRASOUND CONTRAST AGENT

BACKGROUND OF THE INVENTION

Ultrasound contrast agents (UCA) are typically gas-filled microbubbles that are administered intravenously to the systemic circulation. Microbubbles have a high degree of echogenicity, that is, they reflect the ultrasound waves. The echogenicity difference between the gas in the microbubbles and the soft tissue surroundings of the body is immense. Thus, ultrasonic imaging using microbubble contrast agents enhances the ultrasound backscatter, or reflection of the ultrasound waves, to produce a unique sonogram with increased contrast due to the high echogenicity difference. Contrast-enhanced ultrasound can be used to image blood perfusion in organs, measure blood flow rate in the heart and other organs, and has other applications as well.

A series of surfactant-based UCA, composed of sonicated mixtures of non-ionic surfactants which self-assemble around a gaseous core, have been developed (U.S. Pat. No. 5,352,436). One particular agent, ST68, consists of SPAN® 60 (sorbitan monostearate) and TWEEN® 80 (polyoxyethylene sorbitan monooleate) filled with octafluoropropane (a PFC gas) (Basude et al., 2001, Ultrasonics, 39, 437-44). This agent can consistently be produced with a mean size of 1.5 to 2 µm and produces over 20 dB enhancement for doses less than 100 µl/l in vitro (Basude et al., 2000, Ultrasound Med. Biol., 26, 621-8) and 0.05 ml/kg in vivo (Forsberg et al., 1996, 1996, IEEE Ultrasonics Symp., 2, 1337-40). However, further development of this agent is hampered by the fact that it consists of an aqueous suspension of bubbles, which have limited stability with time (less than a week at 4° C. An ideal UCA has been described as being stable at room temperature for at least 6 months (Wang et al., 1996, J. Phys. Chem., 100, 13815-21).

The technique of freeze-drying, or lyophilization, has been implemented to increase the shelf-life and stability of vaccines, viruses, and proteins in pharmaceutical production (Jennings, 1999, Lyophilization: Introduction and Basic Principles. Interpharm. Press. Denver, Colo.) and in liposomes as drug carriers with and without acoustic reflectivity (i.e. increased echogenicity) (Huang et al., 2002, Cell Molec. Biol. Letters, 7, 233-5; Hua et al., 2003, Drying Technol., 21, 1491-505). However, this process generates stresses during the freezing and drying stages which could destabilize the suspension and destroy the bubbles (Abdelwahed et al., 2006a, Euro. Pharm. Biopharm., 63, 87-94). Some agents, such as liposomes, require the addition of cryoprotectants to aid stability during freezing (Ozer et al., 1988, Acta Pharm. Technol., 34, 129-39) or lyoprotectants to help prevent structural and functional integrity loss that occurs during the drying process (Jennings 1999, supra). This is achieved by preventing fusion and aggregation during freeze-drying thus allowing for better reconstitution (Hua et al., 2003, supra). It has been suggested that the major damaging factors associated with freeze-drying liposomes are lipid-phase transition and fusion (Crowe et al., 1997, Cryobiol., 35, 20-30).

In order to be used safely in a clinical setting as well as to access various biological compartments, a contrast agent must have a diameter less than 8 µm. Typically, it has been difficult to fabricate ultrasound contrast agents in the nanometer range that are as functionally effective as their micrometer counterparts. In addition, all microbubble UCA suffer from a lack of stability, and being susceptible to degradation when freeze-thawed. Accordingly, there is an ongoing need in the art for the development of stable ultrasound contrast agents in the sub-micron size-range. There is also a need for an ultrasound contrast agent that is not susceptible to freeze-drying degradation. The present invention fills this need.

BRIEF SUMMARY OF THE INVENTION

Provided is a freeze-dried ultrasound contrast agent (UCA) comprising at least a first surfactant, a second surfactant and a saccharide. In an embodiment, the saccharide is selected from the group consisting of glucose and trehalose.

Also provided is a reconstituted UCA, comprising a freeze-dried UCA and an excipient, wherein the freeze-dried UCA comprises at least a first surfactant, a second surfactant and a saccharide. In an embodiment, the saccharide is selected from the group consisting of glucose and trehalose.

Also provided a particle-stabilized ultrasound contrast agent (UCA) comprising at least a first surfactant and a second surfactant, wherein the first surfactant is d-α-tocopheryl polyethylene glycol 1000 succinate (TPGS), wherein said UCA further comprises a particulate material that stabilizes the UCA, wherein the diameter of said UCA is between 1 nm and 1 µm.

The surfactants of the freeze-dried UCA, reconstituted UCA or particle-stabilized UCA can be selected from the group consisting of SPAN® 60 (sorbitan monostearate), alkylphenol ethoxylate-based surfactants, alcohol ethoxylate-based surfactants, silicone-based surfactants, alkyl poly(ethylene oxide), alkylphenol poly(ethylene oxide), copolymers of poly(ethylene oxide) and poly(propylene oxide), alkyl polyglucosides, fatty alcohols, cocamide MEA, cocamide DEA, and polysorbates. In some embodiments, the first surfactant is TPGS.

In some embodiments of the freeze-dried UCA or reconstituted UCA, the UCA is a particle-stabilized UCA.

Also provided is a method of making a lyoprotected ultrasound contrast agent. The method comprises the steps of a) preparing a UCA comprising at least a first surfactant and a second surfactant; and b) adding a lyoprotectant to the UCA to prepare a lyoprotected UCA, wherein the lyoprotectant is a saccharide. Optionally, the method can further comprise the step of c) freeze-drying the lyoprotected UCA, thereby preparing a freeze-dried UCA. In an embodiment, the saccharide is selected from the group consisting of glucose and trehelose.

A method of making a particle-stabilized ultrasound contrast agent (UCA) is also provided. The method comprises the steps of: a) mixing at least two surfactants in 50 ml of water where one of the surfactants is TPGS and heating the mixture until both surfactants are dissolved; b) cooling the mixture to room temperature while stirring rapidly until the dispersible waxy solid comes out of solution as fine particles; c) purging the mixture using a sterile filtered gas in an ice bath; d) sonicating the mixture at between 100-140 W for 1-5 minutes with constant purging; e) placing mixture in a separation funnel with 50 ml PBS to allow effective separation of the bubbles; f) discarding lower 25 ml of the solution and transferring the next 50-75 ml of solution remaining is placed in a second separation funnel; and g) washing the bubbles of desired size, collecting them, and optionally, freeze drying them for storage.

In the methods of the invention, the surfactants can be selected from the group consisting of SPAN® (sorbitan monostearate), alkylphenol ethoxylate-based surfactants, alcohol ethoxylate-based surfactants, silicone-based surfactants, alkyl poly(ethylene oxide), alkylphenol poly(ethylene oxide), copolymers of poly(ethylene oxide) and poly(propylene oxide), alkyl polyglucosides, fatty alcohols, cocamide MEA, cocamide DEA, and polysorbates. In some embodiments, the first surfactant is TPGS.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, panel A depicts the structure of SPAN® 60 (sorbitan monostearate). FIG. 1, panel B depicts the structure of TWEEN® 80 (polyoxyethylene sorbitan monooleate).

FIG. 5, panel A depicts stabilization of gas bubbles with colloidal particles (the particle size is exaggerated for clarity). FIG. 5, panel B depicts the adsorption of partially-lyophobic particles at the gas-liquid interface. FIG. 5, panel C depicts the approaches used to tune the wetting properties of originally hydrophilic particles to illustrate the universality of the foaming method developed.

(FIG. 15, panel A) and 37° C. (FIG. 15, panel B) temperature. ANOVA testing showed ST68 with glucose at 23° C. to be the only lyoprotected agent statistically greater than that of the ST68 control and all other lyoprotected samples after 15 minutes (*p<0.05, **p<0.01) (f=5 MHz, 684 kPa, PRF=100 Hz).

DETAILED DESCRIPTION OF THE INVENTION

The present invention is related to the discovery that an ultrasound contrast agent (UCA) comprising particle stabilized micro- and/or nanobubbles is more stable compared to an UCA without particles. The invention is further related to the discovery that certain saccharides can function as lyoprotectants for an ultrasound contrast agent subjected to a freeze-dry process. Specifically, the saccharide enables reconstitution of freeze-dried UCA, while substantially preserving the echogenicity observed for non-freeze-dried UCA. Other advantages, including structural stability, storage stability and in vivo dose response are also observed.
Definitions:

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the term "hydrophilic-lipophilic balance" ("HLB") is a relative measure of the ratio of polar and non-polar groups present in a surfactant.

As used herein, "ultrasound contrast agent" ("UCA") refers to surfactant-stabilized gas bubbles.

As used herein, "lyoprotectant" refers to a compound that minimizes or prevents structural and/or functional integrity loss of UCA that can occur during the drying stage of a freeze-drying process.

As used herein, "cryoprotectant" refers to a compound that provides stability during the freezing stage of a freeze-drying process.

Figure 3:
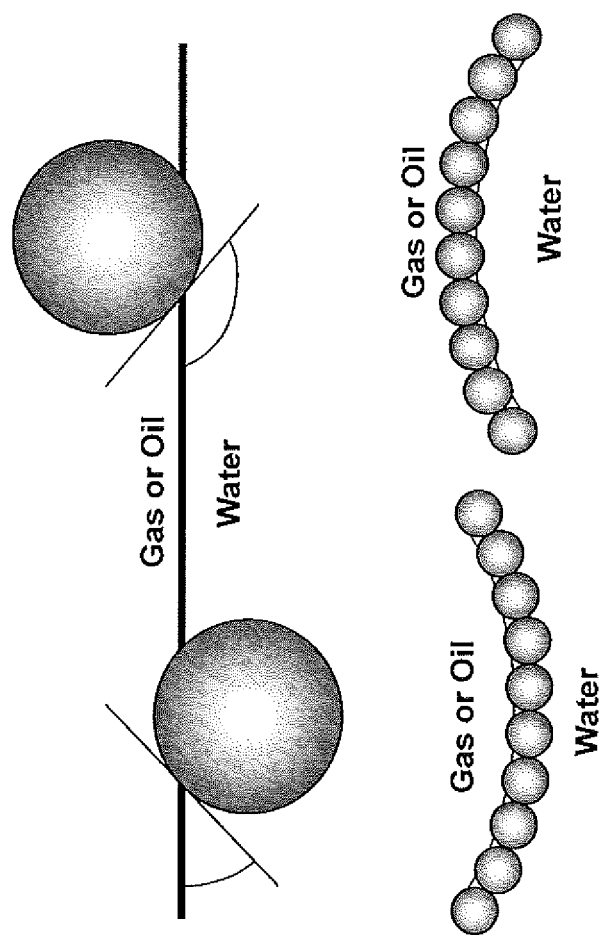
FIG. 3 is a schematic depicting the position of a small spherical particle at the interface for a contact angle θ (measured through the aqueous phase) of less than 90° (left) or great than 90° (right). For θ<90°, solid-stabilized aqueous foam or o/w emulsions may form. For θ>90°, solid-stabilized aerosols or w/o emulsions may form.

It is understood that any and all whole or partial integers between any ranges set forth herein are included herein.
Description:

In one embodiment, the present invention is an ultrasound contrast agent (UCA) comprising stabilized gas bubbles, wherein the gas bubble is stabilized by at least two surfactants, and further wherein one of those surfactants is d-α-tocopheryl polyethylene glycol 1000 succinate (TPGS), also known as vitamin E (FIG. 3). The UCA of the invention are less than 8 micrometer (μm). A preferred size range for the UCA of the invention is between about 1 nanometer (nm) to about 1000 nm, such as between about 1 nm and about 100 nm, between about 100 nm and about 300 nm, between about 300 nm and about 500 nm, between about 300 nm and about 800 nm, and between about 500 nm and about 1000 nm.

Surfactants useful in the practice of the invention are any biocompatible surfactants known in the art including anionic, cationic, zwitterionic, and nonionic surfactants. In a preferred embodiment, the UCA comprises at least one nonionic surfactant. Preferably, the at least two surfactants are both nonionic surfactants. When the surfactant is nonionic, the hydrophilic-lipophilic balance (HLB) of the surfactant is between about 6 and about 16. Non-limiting examples of nonionic surfactants useful in the practice of the invention include, but are not limited to, TPGS, SPAN® (sorbitan monostearate) (e.g., SPAN® 40 (sorbitan monostearate) and SPAN® 60 (sorbitan monostearate)), alkylphenol ethoxylate-based surfactants, alcohol ethoxylate-based surfactants, silicone-based surfactants, alkyl poly(ethylene oxide), alkylphenol poly(ethylene oxide), copolymers of poly(ethylene oxide) and poly(propylene oxide), alkyl polyglucosides, fatty alcohols, cocamide MEA, cocamide DEA, and polysorbates (e.g., TWEEN® 20 (polyoxyethylene sorbitan monooleate) and TWEEN® 80 (polyoxyethylene sorbitan monooleate)).

Figure 1:
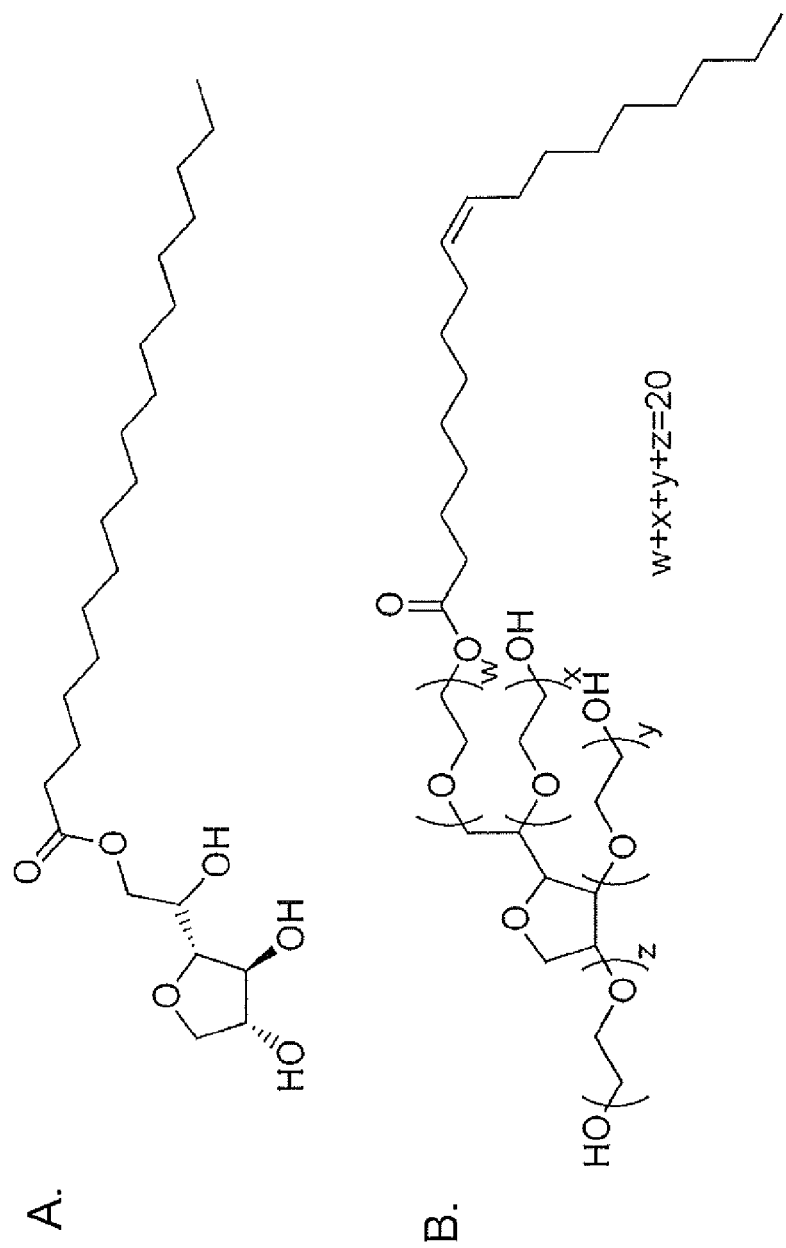
FIG. 1, consisting of panels A and B depict exemplary surfactants.
Figure 7:
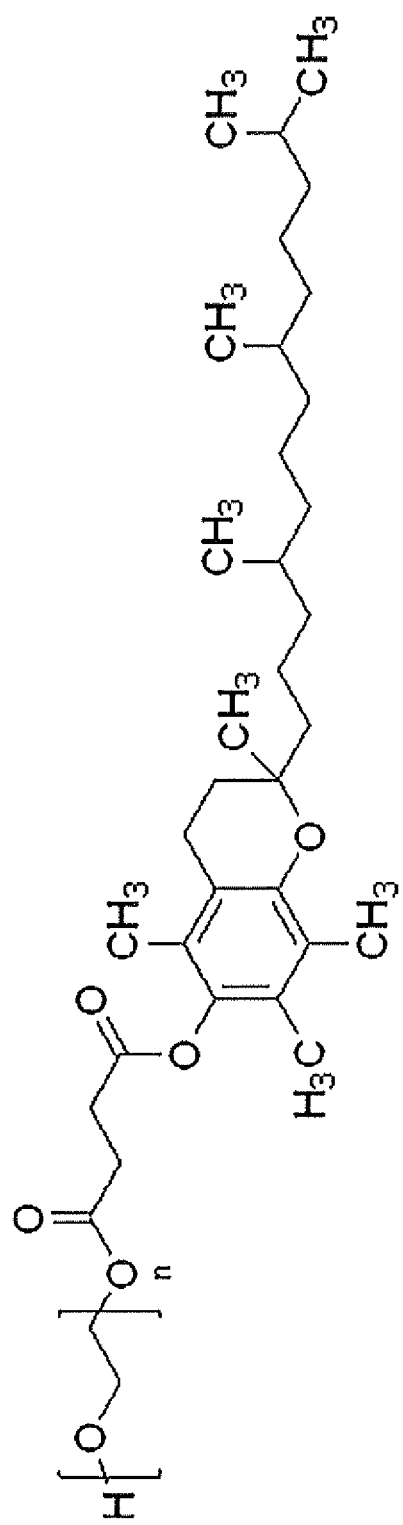
FIG. 7 depicts the molecular structure of d-α-tocopheryl polyethylene glycol 1000 succinate (TPGS).

In some embodiments, the UCA at least two non-ionic surfactants selected from the group consisting of SPAN® (sorbitan monostearate), TWEEN® (polyoxyethylene sorbitan monooleate) and TPGS. The possible compositions in these embodiments include combinations of SPAN® (sorbitan monostearate)/TWEEN® (polyoxyethylene sorbitan monooleate), SPAN® (sorbitan monostearate)/TPGS and SPAN® (sorbitan monostearate)/(polyoxyethylene sorbitan monooleate)/TPGS. The different surfactants in various combinations, in various concentrations, and encapsulating different gases (e.g., air, sulfur hexafluoride ($SF_6$) and perfluorocarbon, (PFC) will dictate the packing density and strength of inter-molecular forces around the gas. In one embodiment, the UCA comprises SPAN® 60 (sorbitan monostearate). SPAN® 60 (sorbitan monostearate) is depicted in FIG. 1A. In one embodiment, the UCA comprises TWEEN® 80 (polyoxyethylene sorbitan monooleate). TWEEN® 80 (polyoxyethylene sorbitan monooleate) is depicted in FIG. 1B. TPGS is depicted in FIG. 7.

The microbubbles and nanobubbles comprising surfactants may be stabilized by the presence of a particulate material. In one embodiment, the particulate material is one of the surfactants. In other embodiments, an exogenous particulate material in incorporated into the UCA. The exogenous particulate material is incorporated any time prior to the sonication step. Examples of particles that are useful in the practice of the invention include, but are not limited to, solid surfactant; quantum dots; colloidal gold; carbon nanotubes; carbon nanotubes containing drug; polystyrene; bucky balls; SPIO (superparamagnetic iron oxide); iron oxide; coated nanoparticles containing a drug; imaging agents such as gas; radiopaque species; MR contrast agents such as Gd compounds; a pure drug in nanoparticulate form (e.g., by grinding); nanocapsules; hollow drug-containing contrast medium containing (CT, MRI, Spect) particles with attached targeting agents such as antibodies, portions of antibodies, peptide sequences etc.; viruses; and inactivated viruses. The particle suitable for use in the invention ranges in size from about 1 to about 500 nm, depending upon the size of the microbubbles and nanobubbles. The contact angle between the material of the particles and the fluid should be less than 90 degrees. (See FIG. 3, left side).

In the following embodiments, the specific volumes recited are exemplary. However, the methods of the invention are not limited to these volumes. In one embodiment, the method of making a particle-stabilized UCA of the instant invention comprises the following steps:

1. At least two surfactants are combined in 50 ml of water where one of the surfactants is TPGS. In one embodiment, the other surfactant comprises a dispersible waxy solid such as SPAN® 60 (sorbitan monostearate) or SPAN® 40 (sorbitan monostearate). The mixture is heated until both surfactants are dissolved. The mixture may then be autoclaved.
2. The mixture is cooled to room temperature while stirring rapidly to allow the dispersible waxy solid to come out of solution as fine particles.
3. In an ice bath, the mixture is purged using a sterile, filtered gas such as PFC or $SF_6$.
4. The mixture is then sonicated at between 70 and 140 W and preferably between 100 and 140 W for 1-5 minutes with constant purging.
5. Contents of the beaker are then placed in a separation funnel with 50 ml PBS to allow separation of the bubbles.
6. After sufficient time to allow separation as determined by the skilled artisan, the lowest 25 ml of the solution (e.g., about 25% of total solution) is discarded and the next 50-75 ml of solution remaining is placed in a second separation funnel. The mixture remaining in the first funnel contains micron sized bubbles. The mixture in the second funnel contains nano-sized bubbles.
7. The mixture in both funnels is washed and the bubbles of the desired size collected. The bubbles are optionally freeze dried according to methods described elsewhere herein.

In another embodiment, the method is practiced as follows:

1. 1.5 g of sodium chloride and 1.464 g of a dispersible waxy solid, such as SPAN® 60 (sorbitan monostearate) or SPAN® 40 (sorbitan monostearate), and 1.288 g of TPGS are added to 50 mL of PBS and the mixture is stirred.
2. The mixture is slowly heated with continuous stirring to bring to boiling, and dissolve the solid and TPGS.
3. The mixture is autoclaved with the stir bar in place for 20-35 min.
4. The mixture is allowed to cool to room temperature for 30-45 minutes while rapidly stirring so that the SPAN® (sorbitan monostearate) comes out of solution as fine particles.
5. Two 125 ml sterile separation funnels are set up in that cold room to cool to 4° C.
6. The beaker is placed in an ice bath and purged with sterile filtered gas, such as PFC or $SF_6$ gas, until bubbles cover the solution before sonication. When purging with gas, the tip that supplies the gas will be in the solution.
7. The mixture is sonicated at between 70 and 140 W and preferably between 100 and 140 W for 1-5 minutes (Misonix Inc. CL4 tapped horn probe with 0.5" tip, Farmingdale, N.Y.) with constant purging using a steady stream of gas of choice. When sonicating, the tip supplying the gas is not in the solution; only the sonication probe will be submerged.
8. The contents of the beaker are poured into one of the separation funnels (designated funnel A), along with by 50 mL cold PBS. The separation funnel is place in the fridge for about one hour, or long enough to allow separation of the bubbles according to size to occur.
9. After about 1 to about 2 hours, the lower 25 ml of solution is discarded and the next 50-75 ml of the solution is transferred to the second cold separation funnel (designated funnel B).

At this stage separation funnel A contains the majority of micron sized bubbles and funnel B contains the majority of nano sized bubbles.

Funnel A
1) The contents of funnel A are washed twice with 50 ml PBS, allowing 35-50 minutes to elapse between each wash for separation of the bubbles according to size. After each wash, the middle layer containing predominantly micron sized bubbles is collected, and the lower portion of the mixture is discarded.

Funnel B
1) The contents of funnel B are washed twice with 50 ml PBS, allowing about one hour to elapse between each wash for separation of the bubbles according to size. Twenty ml of solution is discarded from the bottom of the separating funnel. After the second wash, 10 ml of nanobubbles is collected.

Both nanopreparations are then taken forward for either freeze drying or storage at 4° C. For cold storage, samples are either taken up into vacutainer tubes which are completely filled, or placed in glass vials, which are tightly capped only after the head space has been purged with the filling gas (e.g., PFC or $SF_6$). These vials are stored at 4° C.

It will be understood by the skilled artisan that standard sterile techniques may be used throughout the procedure in order to produce a sterile composition comprising the particle stabilized UCA of the instant invention.

The particle-stabilized UCA may be freeze-dried according to method described elsewhere herein for storage and later reconstituted using a pharmaceutically acceptable carrier. As used herein, the term "pharmaceutically acceptable carrier" means a chemical composition with which the active ingredient may be combined and which, following the combination, can be used to administer the active ingredient to a subject.

Although the descriptions of pharmaceutical compositions provided herein are principally directed to pharmaceutical compositions which are suitable for ethical administration to a subject where the subject is a human, it will be understood by the skilled artisan that such compositions are generally suitable for administration to animals of all sorts.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

A pharmaceutical composition comprising a UCA of the invention, such as a particle stabilizes UCA, may be administered to a subject parenterally. As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous administration.

In another embodiment, the invention provides a method for freeze-drying surfactant-stabilized gas bubbles while substantially preserving the echogenicity and stability of the bubbles. Also provided are freeze-dried surfactant-stabilized gas bubbles and reconstituted freeze-dried surfactant-stabilized gas bubbles.

The method comprises adding a saccharide to a UCA prior to freeze-drying the UCA. The saccharide is preferably one of glucose or trehalose. Most preferably, the saccharide is glucose. In an non-limiting exemplary example, a UCA, such as ST68, is diluted in 1:1 by volume with a solution of the saccharide. The final concentration of the saccharide in the mixture with the UCA can be from about 1 millimolar (mM) to less than about 200 mM, preferably from about 10 mM to about 140 mM, and more preferably about 50 mM to about 100 mM. In a preferred embodiment, the final concentration of the saccharide is about 90 to about 110 mM in the mixture with the UCA. The mixture is then flash frozen, for instance, in liquid nitrogen, and then dried at a temperature of about −80° C. to about −70° C. The container comprising the resulting freeze-dried UCA is then purged, for instance with octafluoropropane gas, and the containers are sealed to prevent exposure of the lyophilized UCA to atmosphere.

UCA described herein can be reconstituted with any gas of choice, including, but not limited to, air, PFC or $SF_6$. An exemplary method of freeze drying and filling UCA with gas is as follows. An aliquot of a UCA suspension is placed in a 15 ml lyophilization vial (West Pharmaceutical Services, Lionville, Pa.). A FLUOROTEC® lyophilization stopper (West Pharmaceutical Services) is placed in the neck of the vial up to the first groove. The agent is then flash frozen in liquid nitrogen. The vial is placed on a previously chilled (initially to −80° C.) two-shelf stoppering rack of a VIRTIS® benchtop freeze-dryer (Gardiner, N.Y.) and freeze dried at pressures below 300 par and a condenser temperature of −76° C. For gas filling, the piston of the stoppering rack is lowered prior to venting the freeze dryer, thus sealing the stopper in the vial under vacuum. The stoppered vial is removed from the freeze dryer, and the gas of choice is introduced into the individual vial from a tank via a needle pierced through the stopper septum. A gas flow rate of 50 ml/min for the first 5 to 10 seconds and then 20 ml/min for the next minute can be used to insure the vial is filled. For capsules filled with air, the freeze drier is vented to the atmosphere prior to stoppering the vials.

As shown herein, the freeze-dried UCA advantageously is shelf stable for extended periods of time. Upon reconstitution, for instance with phosphate buffered saline, the reconstituted UCA retains a substantial degree of echogenicity as compared to a non-lyophilized UCA. In some embodiments, the reconstituted UCA has at least about 50%, 55%, 60%, 65%, 70%, or 75% of the enhancement exhibited by the same UCA that is freshly prepared and not subjected to lyophilization. In some embodiments, the reconstituted UCA has at least about 80% of the enhancement exhibited by the same UCA that is freshly prepared and not subjected to lyophilization. The reconstituted freeze-dried UCA of the invention also possesses stability comparable to the same UCA that is freshly prepared and not subjected to lyophilization.

In an embodiment of the method, the UCA is ST68, optionally particle stabilized, and lyoprotected with 100 mM glucose (ST68G-100). Exemplary methods of making ST68 are known in the art (U.S. Pat. No. 5,352,436; Wheatley et al., 1995, Reactive Polymers, 25, 157-66; Wheatley et al., 2006, Ultrasound Med. Biol., 32, 83-93). Reconstitution of lyophilized ST68G-100 provides an UCA providing an in vitro peak US enhancement of over 20 dB (37° C.; 5 MHz), with a half-life of about 2.5 minutes and having measurable echogenicity for at least about 5 minutes and preferably at least about 10 minutes.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Experimental Examples 1-4

The materials and methods employed in Examples 1-4 disclosed herein are now described.

Surfactants

The surfactants for this study are three non-ionic surfactants, of which two surfactants are fatty acid esters of sorbitan (SPAN® (sorbitan monostearate) and TWEEN® (polyoxyethylene sorbitan monooleate)) and the third is water soluble vitamin E, (d-α-tocopheryl polyethylene glycol 1000 succinate: TPGS). The potential compositions include combinations of SPAN® (sorbitan monostearate)/TWEEN® (polyoxyethylene sorbitan monooleate), SPAN® (sorbitan monostearate)/TPGS and SPAN® (sorbitan monostearate)/TWEEN® (polyoxyethylene sorbitan monooleate)/TPGS. The different surfactants in various combinations, in various concentrations, and encapsulating different gases (air, sulfur hexafluoride ($SF_6$) and perfluorocarbon, (PFC) will dictate the packing density and strength of inter-molecular forces around the gas. The agents will be optimized/characterized in vitro for stability and echogenicity.

A mixture of two non-ionic surfactants, SPAN® (sorbitan monostearate) and TWEEN® (polyoxyethylene sorbitan monooleate), was used to stabilize gas bubbles. Both surfactants are fatty acid esters of sorbitan, which can have a hydrophobic tail group, for example monolaurate (C11: SPAN® 20 (sorbitan monostearate) and TWEEN® 20 (polyoxyethylene sorbitan monooleate)), monopalmitate (C15: SPAN® 40 (sorbitan monostearate) and TWEEN® 40 (polyoxyethylene sorbitan monooleate)), monostearate (C17: SPAN® 60 (sorbitan monostearate) and TWEEN® 60 (polyoxyethylene sorbitan monooleate)), and monooleate (C17: SPAN® 80 (sorbitan monostearate) and TWEEN® 80 (polyoxyethylene sorbitan monooleate)). All chains are fully saturated except for the oleate chains which contain a single double-bond. The difference between TWEEN® (polyoxyethylene sorbitan monooleate) and SPAN® (sorbitan monostearate) is that TWEEN® (polyoxyethylene sorbitan monooleate) has the hydrophilic sorbitan head group modified with polyethyleneoxide groups (see FIG. 1) and this greatly increases polarity that makes the molecule more water-soluble. It should be noted that the stable microbubbles are successful only in the combination between solid SPAN® (sorbitan monostearate) (SPAN® 40 (sorbitan monostearate) and SPAN® 60 (sorbitan monostearate)) and almost all types of TWEEN® (polyoxyethylene sorbitan monooleate). The trioleate series of SPAN® 85 (sorbitan monostearate) and TWEEN® 85 (polyoxyethylene sorbitan monooleate) do not stabilize bubbles in any combination, which is expected since their oleate fatty acid chains are extremely bulky (Table 1; Wheatley et al., 1995, supra). Also, different combinations of surfactant and different gases affect the backscatter from the microbubbles (Forsberg et al., 1999, Ultrasound in Med. And Biol. 25:1203-1211).

tant molecules do when they form micelles, and, hence the solubilization phenomena (i.e. the ability of dilute surfactant solutions to solubilized water-insoluble substances to form stable systems; Harris, 1958, J. Am. Oil Chem. Soc. 35:428-435) is absent in the particle case. When the spherical particles adsorb to interfaces, the contact angle θ which the particle makes with the interface is important (Binks, 2002, supra). For hydrophilic particle, the contact angle measured into the aqueous phase is normally less than 90° and the larger fraction of the particle resides in the water. By analogy with surfactants, the monolayer will curve to make the larger area of the particle surface remain on the external side, giving rise to air or oil-in-water emulsions for θ<90° (FIG. 3). There will be an opposite effects for hydrophobic particles, which are suitable for water-in-air or water-in-oil emulsions with a contact angle which is greater than 90° (FIG. 3).

For the particle-stabilized foams, the stability is proportional to particle concentration and inversely proportional to particle size. This is because smaller particles in high concentrations form a more complete layer thus giving the most effective steric barrier.

The physical reason for the better efficiency of particles over surfactants in stabilizing foams is their attachment energy, which can be up to several thousand kT per particle, where k is the Boltzmann constant and T is the absolute temperature, compared to only a few kT per surfactant molecule (Dickinson et al., 2004, Langmuir 20:8517-8525). Because of this high energy attachment at the interface, the particle adsorption can be considered as irreversible (Vignes-Adler et al., 2008, Current Opinion in Colloids & and

TABLE 1

|  | SPAN® 60 (sorbitan monostearate) (solid) 4.7[a] | SPAN® 40 (sorbitan monostearate) (solid) 6.7 | SPAN® 20 (sorbitan monostearate) (liquid) 8.6 | SPAN® 80 (sorbitan monostearate) (liquid) 4.3 | SPAN® 85 (sorbitan monostearate) (liquid) 1.8 |
|---|---|---|---|---|---|
| TWEEN® 20 (polyoxyethylene sorbitan monooleate) (liquid) 16.7[a] | Y | Y | N | N | N |
| TWEEN® 40 (polyoxyethylene sorbitan monooleate) (liquid) 15.6 | Y | Y | N | N | N |
| TWEEN® 60 (polyoxyethylene sorbitan monooleate) (liquid) 14.9 | Y | Y | N | N | N |
| TWEEN® 65 (polyoxyethylene sorbitan monooleate) (solid) 10.5 | Y | Y | N | N | N |
| TWEEN® 80 (polyoxyethylene sorbitan monooleate) (liquid) 15.0 | Y | Y | N | N | N |
| TWEEN® 85 (polyoxyethylene sorbitan monooleate) (liquid) 11.0 | N | N | N | N | N |

Y: microbubbles were formed,
N: microbubbles were not formed.
[a]HLB values.

Figure 2:
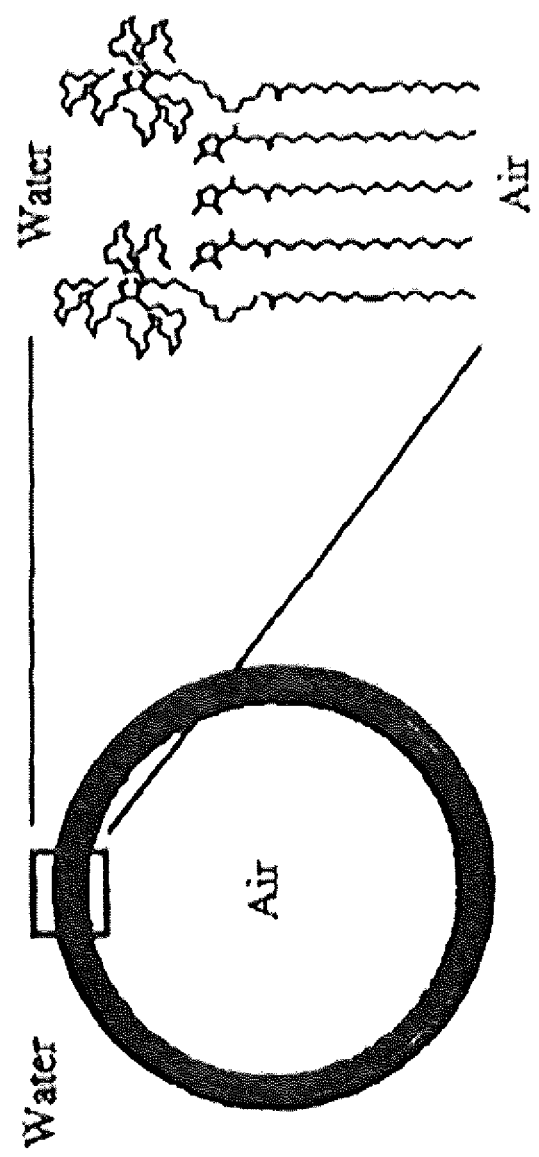
FIG. 2 is a schematic diagram depicting a previously proposed model for microbubbles stabilized by SPAN® 60 (sorbitan monostearate) and TWEEN® 80 (polyoxyethylene sorbitan monooleate).

The previous model for microbubbles stabilized by SPAN® 60 (sorbitan monostearate) and TWEEN® 80 (polyoxyethylene sorbitan monooleate) is shown in FIG. 2, and was developed using a Langmuir trough. The model suggested that the stability of the bubble is due to the fact that the bulky head of TWEEN® (polyoxyethylene sorbitan monooleate) is stabilized by the presence of SPAN® (sorbitan monostearate) in the shell which causes the reduction of the repulsive force in TWEEN® (polyoxyethylene sorbitan monooleate) molecules by hydrophobic attraction between the tail groups. This model, however, cannot explain why the microbubbles are stable only with solid SPAN® (sorbitan monostearate).

Particle-Stabilized Foams

Figure 4:
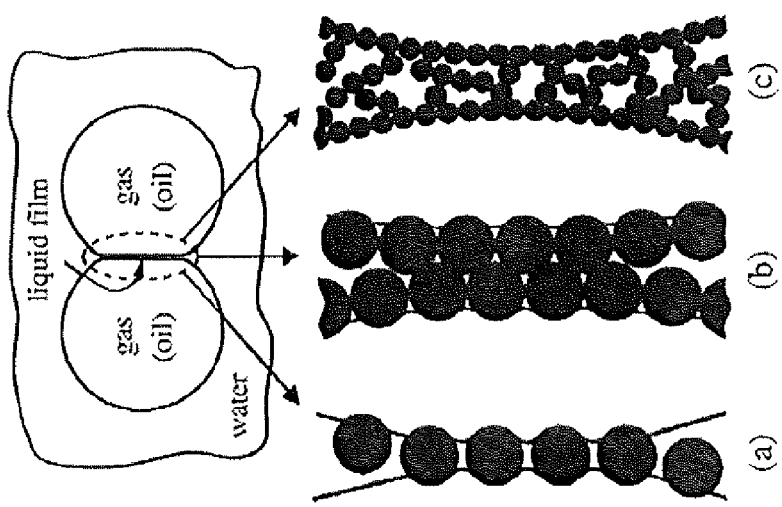
FIG. 4 is a schematic diagram depicting possible mechanisms of liquid film stabilized by: (a) a monolayer of particles; (b) a bilayer of close-packed particles and (c) a network of particle aggregated inside the film.

Particles can act as surfactants in stabilizing foams and emulsions (Binks, 2002, Curr. Opin. Colloid. Interface Sci. 7:21-41; Gonzenbach et al., 2006, Chem. Int. Ed. 45:3526-2530; Hunter et al., 2008, Adv. Colloid Int. Sci. 137:57-81). The solid particles can function in the same ways as surfactants, but some behaviors are different. For example, particles do not always assemble the same way that surfac- Interface Science 13:141-149. The required energy to remove the particle from its equilibrium position at the interface to the bulk liquid phases is $$\Delta G_{remove} = \pi R^2 \sigma (1 \pm \cos \theta)^2 \quad (1)$$

where R is the radius of the spherical solid particle; a is the interfacial energy; θ is the contact angle; sign '+' refers to particle removal into gas phase, while sign '−' refers to the removal into the liquid phase (Kaptay, 2006, Colloids and Surfaces A: Physicochem. Eng. Aspects 282-283:387-401). Equation 1, however, does not say anything about the stability of the thin liquid layer between bubbles which are stabilized by particles. To answer this question, the maximum capillary pressure was introduced and can be calculated from $$\Delta G_{remove} = \pi R^2 \sigma (1 \pm \cos \theta)^2 \quad (2)$$

where p and z are the parameters for different particle arrangements (see FIG. 4). For example, in the case of closed-pack bilayer, if θ<90°, p=4.27 and z=0.405 but for 90°<θ<129.3°, p=2.73 and z=0.633. With Equations 1 and 2, Kaptay can make the calculations that agree with the experimentally observed optimum contact angle interval (Kaptay, 2006, ibid.).

Figure 5:
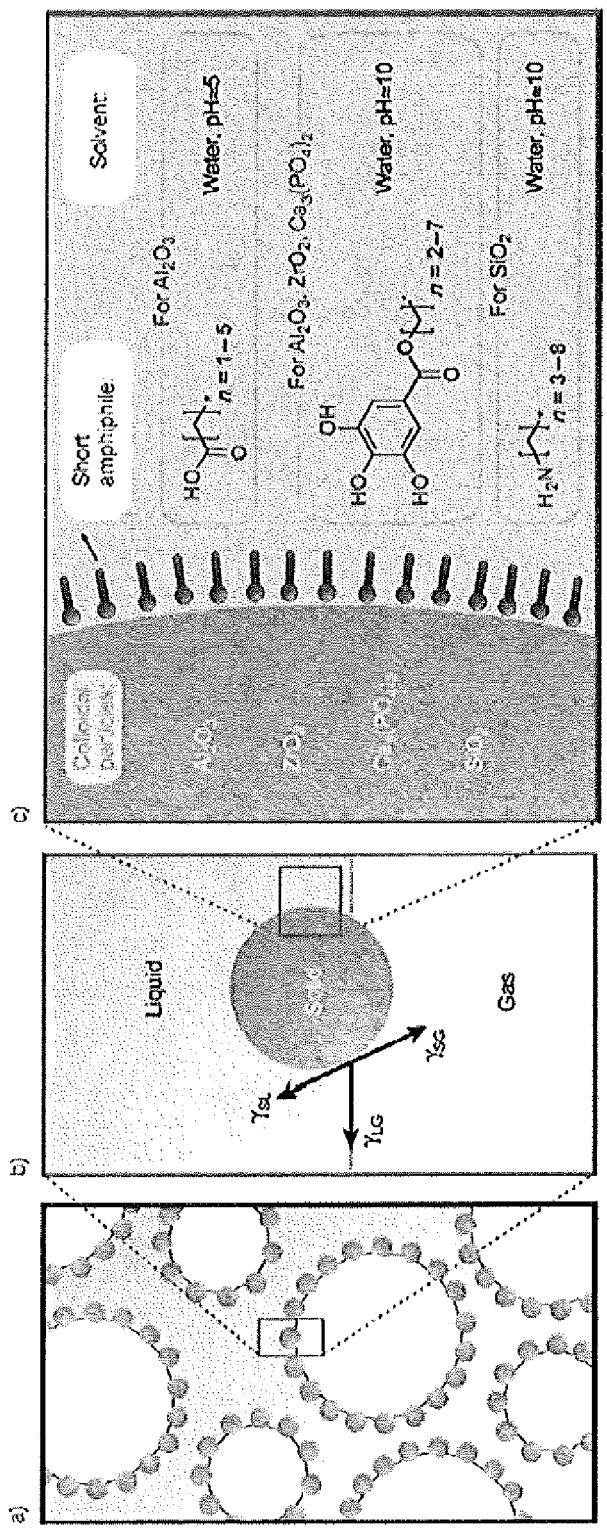
FIG. 5, consisting of panels A-C are a series of images depicting possible approaches to attach colloidal particles at gas-liquid interfaces by tuning their surface-wetting properties.
Figure 6:
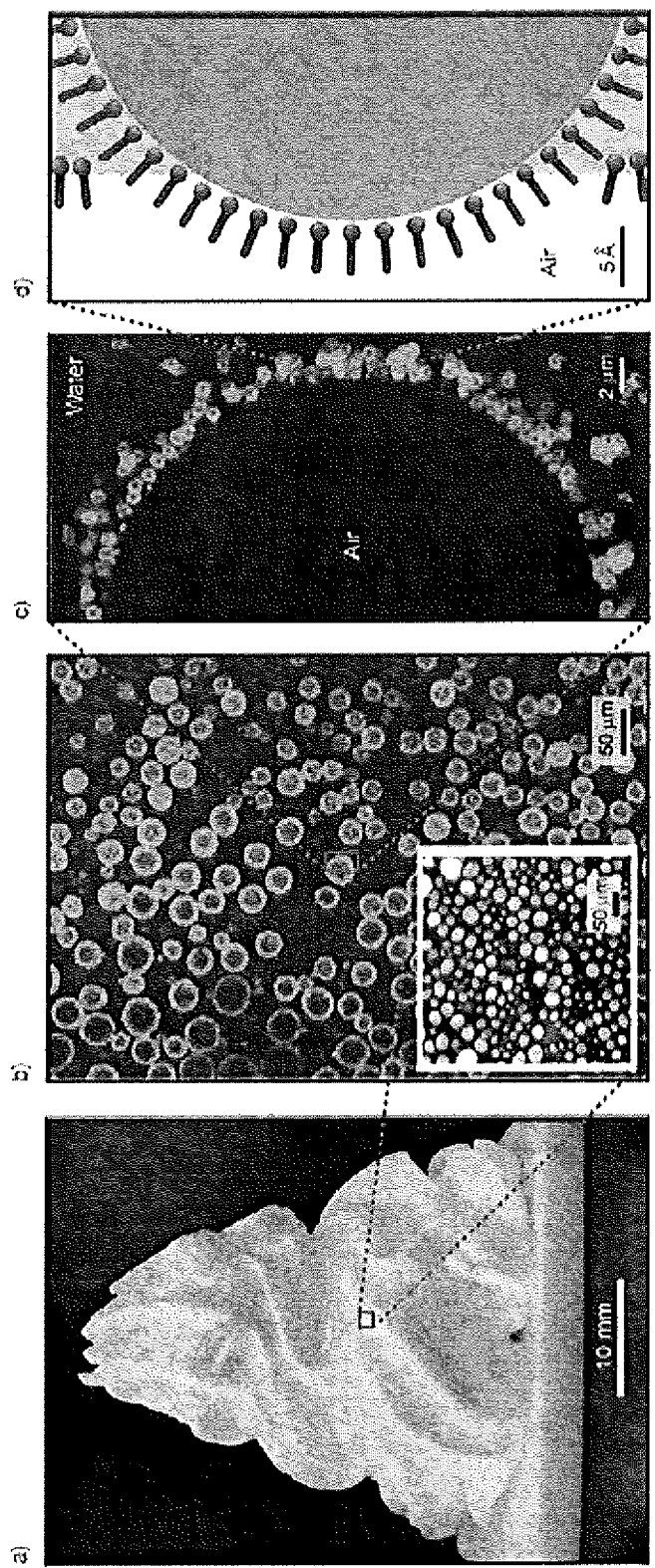
FIG. 6, consisting of panels A-D are a series of images depicting the hierarchical features of particle-stabilized foams containing short amphiphilic molecules. High-volume macroscopic foams (depicted in FIG. 6, panel A) with bubble sizes within the range 10-50 mm (depicted in FIG. 6, panel B) are formed through the adsorption of submicrometer-sized colloidal particles at the air-liquid interface (depicted in FIG. 6, panel C). Particles attach at the air-water interface as a result of the surface hydrophobicity imparted by the adsorbed amphiphilic molecules, as indicated schematically in FIG. 6, panel D. The confocal images shown in FIG. 6, panel B and FIG. 6, panel C were obtained after dilution of concentrated foams (inset in FIG. 6, panel B) containing fluorescently-labeled silica particles and hexylamine as amphiphile.

Another approach to particle-stabilized foams is by changing the hydrophilicity and wetting properties of the solid particles so as to favor their attachment at the gas-liquid interface. One possibility is mixing the colloid particles with amphiphilic molecules or surfactant. This scenario should fit well in our study using the particle of SPAN® (sorbitan monostearate) mixed with TWEEN® (polyoxyethylene sorbitan monooleate). The model and picture of this type of the system are shown in FIGS. 5 and 6.

Vitamin E TPGS (d-α-tocopheryl polyethylene glycol 1000 succinate; TPGS)

Figure 8:
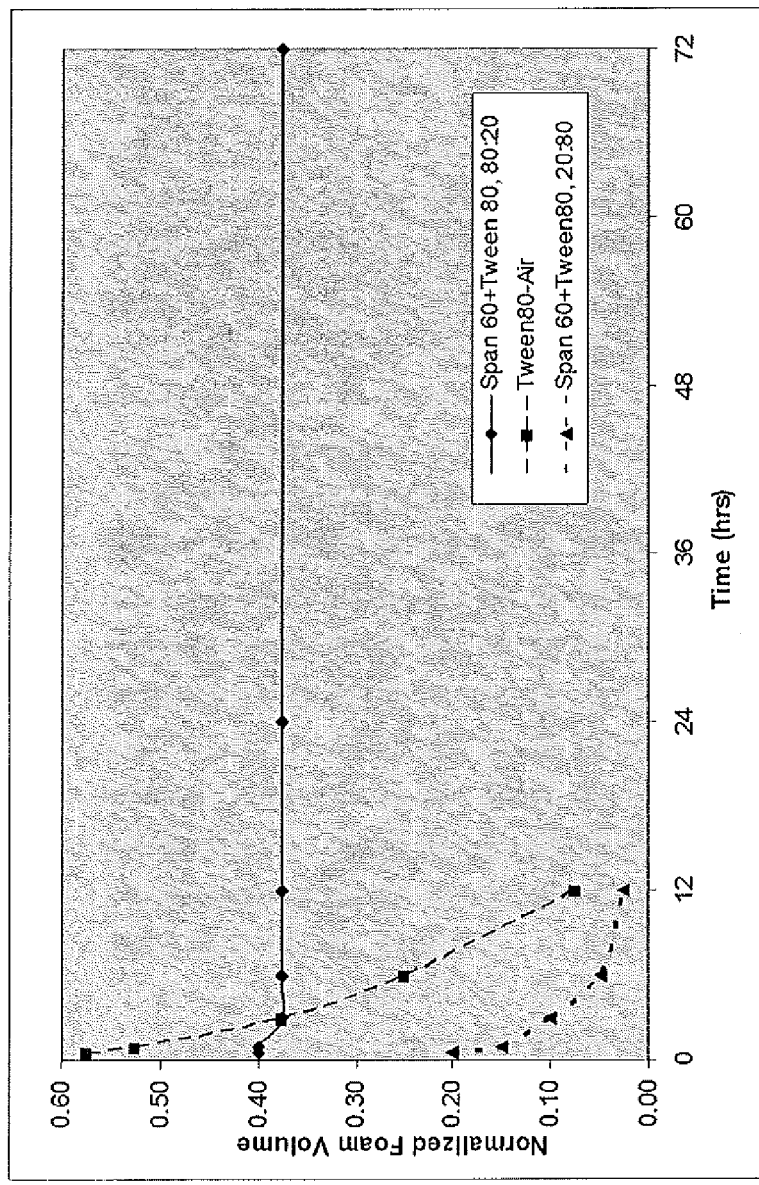
FIG. 8 is a graph depicting the normalized foam volume of TWEEN® 80 (polyoxyethylene sorbitan monooleate) (solid squares) and the mixture SPAN® 60 (sorbitan monostearate) and TWEEN® 80 (polyoxyethylene sorbitan monooleate) at the molar ration of 20:80 (solid triangles) and 80:20 (solid diamonds) over time. The initial concentration of surfactant is 85.1 mM.

TPGS is a water-soluble form of natural source vitamin E. It is very stable and does not hydrolyze under normal conditions. TPGS can be prepared by esterifying the acid group of d-alpha-tocopheryl acid succinate with polyethylene glycol 1000. The molecular structure of TPGS is shown in FIG. 8. It can be used as an emulsifier, drug solubilizer, absorption enhancer, and as a vehicle for lipid-base drug-delivery formulations.

Nile Red

A hydrophobic dye, Nile Red, is a popular fluorescent probe in biological and medical research used to localize and quantify lipids, to stain proteins, and to detect ligand-binding to enzymes. It is also used as a florescent dye probe for the study of micelles (Maiti, et al., 1997, J. Phys. Chem. B 101:11051-11060; Krishna, 1999, J. Phys. Chem. A 103: 3589-3595; Nagy et al., 2003, J. Phys. Chem. A 107:8784-8790). Another interesting property of Nile Red is that its fluorescence is strongly dependent on the polarity of its environment (Sackett et al. Wolff, 1987, Analytical Biochemistry 167:228-234). In DMSO, Nile red has Abs/Em=552/636 nm. In cholesterol ester droplets or hydrocarbon solvents, Nile red fluoresces yellow-gold (528 nm), while in ethanol or phosphatidylcholine vesicles, the dye fluoresces red (>610 nm; Greenspan et al., 1985, Journal of Lipid Research 26:781-789). In aqueous media, it is relatively insoluble and fluorescence is strongly quenched.

Type of Gases

Different types of gases including but not limited to, air, $SF_6$ and PFC, which have a different molecular weights, hydrophobicity, and water solubility, may be used.

In Vivo Acoustic Testing

Dose response curves were generated in 3 kg New Zealand white rabbits with 200 mM glucose stabilized freeze-dried ST68 ("ST68-g"). Each rabbit was sedated with 35 mg/kg ketamine and 3.5 mg/kg xylazine. Increasing volumes from 0.005, 0.01, 0.05, 0.1, to 0.15 mL/kg were injected through an angiography catheter inserted in the left ear vein, followed by a flush with 5 ml of sterile saline. A total of 3 rabbits were used. Roughly 5 to 10 minutes passed between each dose to ensure total destruction of the agent and return to baseline values. A SONIX® RP (Ultrasonix, Richmond, BC, Canada) scanner recorded all data received by the L14-5 linear array set to 5 MHz with a PRF of 6.7 kHz and a gain of 44% on pulse Doppler mode. This transducer was focused on the midabdominal aorta. Pulse inversion, with a power of −8 dB and a PRF of 1 kHz, was used to image the kidney with a dose of 0.1 mL/kg. These studies were carried out under the guidance of a veterinarian and all protocols were approved by Jefferson University's Animal Care and Use Committee. A similar dose curve was previously generated with freshly-prepared ST68.

Size Characterization

All size measurements were carried out using a ZETA-SIZER® NANO ZS™ (Malvern Inst, Worcestershire, UK). Twenty-five μL of agent was dispersed into 975 μL of PBS and gently inverted to ensure thorough mixing. For each sample, three measurements were taken and averaged together. The recorded value is the average±SEM (standard error of the mean) of the z-average value.

Morphological Examination

ST68 g and ST68 (freeze-dried without lyoprotectant) were prepared on an aluminum specimen mount having excess blown off with pressurized air. Samples were carbon coated for 8 seconds using a CRESSINGTON™ 208 benchtop carbon evaporator (Watford, England). Images were taken with a ZEISS® SUPRA™ 50 scanning electron microscope (S.E.M.) with OXFORD ENERGY DISPERSIVE MICROANALYSIS™ (EDS) (Minnesota, USA) set to 3.5 kV and an aperture of 4 mm.

Statistical Analysis

All data is presented as mean±SEM with all experiments repeated at least 3 times (n=3). For all data, statistical significance was determined using a one way ANOVA with a Newman-Keuls post test assuming normal distribution and focusing in on comparisons with controls. All testing was preformed using Prism PRISM™ 3.0 (GraphPad, San Diego, Calif.) using a probability value cut off of 0.05 to determine statistical significance.

The results of Experimental Examples 1-4 are now described.

Experimental Example 1

Particle Stabilized Microbubble Foams as Ultrasound Contrast Agents

It was observed that stable microbubbles can be formed only with a solid SPAN® (sorbitan monostearate), i.e. SPAN® 40 (sorbitan monostearate) and SPAN® 60 (sorbitan monostearate), mixing with TWEEN® (polyoxyethylene sorbitan monooleate). The mixture of SPAN® 20 (sorbitan monostearate), a liquid form, with TWEEN® (polyoxyethylene sorbitan monooleate) or TWEEN® (polyoxyethylene sorbitan monooleate) alone did not give stable microbubbles, which agrees with the study of Wheatley and Singhal, 1995, Reactive Polymers 25:157-166. For this reason, it is possible that the stability of gas bubbles can be modeled as solid particle-stabilized bubbles not a mixture of free surfactants.

The foam can be prepared by adding the desired amount of surfactant(s) to 25 ml phosphate buffered saline (PBS). The solution is then stirred and heated for 3-5 min until boiling or until the surfactant(s) is completely dissolved. The solution is then sterilized for 35 min at which point it is cooled to room temperature. To generate the foam, the 15 ml of the solution is sonicated at maximum power for 3 min. The 20 ml of foam is pour into 25 ml graduated cylinder and amount of foam volume is measure at various times.

After autoclaving and cooling down to room temperature, the solutions of pure TWEEN® (polyoxyethylene sorbitan monooleate) and of low molar ratio of SPAN® (sorbitan monostearate) and TWEEN® (polyoxyethylene sorbitan monooleate) mixtures (i.e. 10:90 and 20:80) were clear compared with solution using higher ratios (e.g., higher than 30:80), which had a milky appearance. Size analysis of the pure TWEEN® (polyoxyethylene sorbitan monooleate) and a low ratio of SPAN® (sorbitan monostearate) to TWEEN® (polyoxyethylene sorbitan monooleate) solutions showed the same size distribution (mean diameter of between 8-10 nm), which is in the micelle range, compared with the mean diameter of higher ratios of SPAN® (sorbitan monostearate) to TWEEN® (polyoxyethylene sorbitan monooleate) that produced particles with more than 100 nm diameter. In the case of low SPAN® (sorbitan monostearate) to TWEEN® (polyoxyethylene sorbitan monooleate) ratios, without wishing to be bound by theory, it is possible that the TWEEN® (polyoxyethylene sorbitan monooleate) in the mixture might increase the solubility of SPAN® (sorbitan monostearate) by formation of mixed micelles. This interpretation agrees with a study by Eiser et al., (2007, Chem. Eng. Sci. 62:1974-1987), which shows increasing solubility of a hydrophobic component (e.g., fat particles) in the presence of a water-soluble surfactant. In the case of the high SPAN® (sorbitan monostearate) to TWEEN® (polyoxyethylene sorbitan monooleate) ratios, there is not enough TWEEN® (polyoxyethylene sorbitan monooleate) to form mixed micelles with SPAN® (sorbitan monostearate), and TWEEN® (polyoxyethylene sorbitan monooleate) adsorbs onto the SPAN® (sorbitan monostearate) particles, stabilizing the SPAN® (sorbitan monostearate) particles while the solution cools down to room temperature after the sterilization. In this way, small particles of SPAN® (sorbitan monostearate) are formed by preventing the aggregation of SPAN® (sorbitan monostearate) particles, and the solutions appear cloudy.

Pictures were taken at periods up to 12 hours after foam was produced by sonicating solutions of pure TWEEN® 80 (polyoxyethylene sorbitan monooleate) (i.e. the pure, single surfactant-stabilized foams) and the mixture of SPAN® 60 (sorbitan monostearate) and TWEEN® 80 (polyoxyethylene sorbitan monooleate) in the molar ratio of 80:20 (i.e. the particle-stabilized foams). It was observed that the surfactant stabilized-foam of pure TWEEN® 80 (polyoxyethylene sorbitan monooleate) is less stable compared with the particle-stabilized foam of the mixture of 80:20 of SPAN® 60 (sorbitan monostearate) to TWEEN® 80 (polyoxyethylene sorbitan monooleate). For the surfactant-stabilized foam (i.e. pure TWEEN® 80 (polyoxyethylene sorbitan monooleate) and the mixture of SPAN® 60 (sorbitan monostearate) and TWEEN® 80 (polyoxyethylene sorbitan monooleate) at molar ratio of 20:80), the foam volume reduces to less than 10% of initial volume exponentially, within 12 hours. In the case of particle-stabilized foam (i.e. the mixture of SPAN® 60 (sorbitan monostearate) and TWEEN® 80 (polyoxyethylene sorbitan monooleate) at molar ratio of 80:20), the foam is very stable, dropping to 37.5% of initial volume and remaining at that volume for even more than 3 days.

Figure 9:
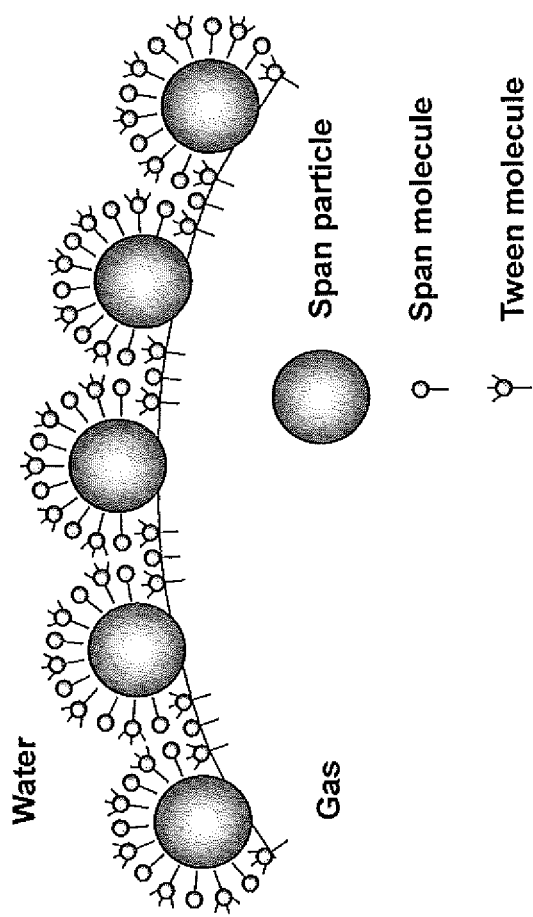
FIG. 9 is a schematic diagram depicting a model for the bubbles stabilized by SPAN® (sorbitan monostearate) and TWEEN® (polyoxyethylene sorbitan monooleate).

Without wishing to be bound by any particular theory, it is hypothesized that particles of SPAN® (sorbitan monostearate) stabilize the bubbles. A possible model could be an adaptation of the models that were originally proposed and is shown in FIGS. 5 and 6. It is proposed that the TWEEN® 80 (polyoxyethylene sorbitan monooleate) molecules stabilize the system by adsorbing around and between the hydrophobic SPAN® 60 (sorbitan monostearate) particles and the solution while part of the SPAN® 60 (sorbitan monostearate) particles should be additionally stabilized while in contact with the hydrophobic gas (FIG. 9).

A Standard Procedure Producing Microbubbles

To fabricate the microbubbles, the desired amount of SPAN® (sorbitan monostearate) with TWEEN® (polyoxyethylene sorbitan monooleate), and, optionally, sodium chloride are added into 50 ml PBS. The solution is then stirred and heated for 3-5 min. until boiling or until SPAN® (sorbitan monostearate) is dissolved. The solution is then sterilized for 35 minutes after which it is cooled to room temperature. To generate the bubbles, the cooled solution (held in an ice bath) is sonicated at 110 W for 3 min in the presence of the desired gas to be entrapped. The bubbles are then washed three times with 50 ml PBS in a separating funnel. The solution is allowed to separate into three distinct layers (about 35 minutes) and the bottom layer consisting of unused surfactants is discarded with each wash. After the last wash, the microbubbles at the middle layer are collected.

The microbubbles are named after the mixture of SPAN® (sorbitan monostearate) and TWEEN® (polyoxyethylene sorbitan monooleate) that is used. For example, ST44 consists of SPAN® 40 (sorbitan monostearate) and TWEEN® 40 (polyoxyethylene sorbitan monooleate), ST48 consist of SPAN® 40 (sorbitan monostearate) and TWEEN® 80 (polyoxyethylene sorbitan monooleate) and ST68 consist of SPAN® 60 (sorbitan monostearate) and TWEEN® 80 (polyoxyethylene sorbitan monooleate). One of the beauties of the agent is the range of combinations that is possible.

Acoustic Testing

The acoustic properties of microbubbles were tested in vitro by an acoustic set up. A one-dimensional pulsed A-mode US set-up with a single element, broadband, 12.7 mm element diameter, 50.8 mm spherically focused transducers with center frequencies of 5 MHz (Panametrics, Inc., Waltham, Mass.). The −6 dB bandwidths of the transducers were 89%, 92%, 71% and 65%, respectively. The transducers were inserted in a water bath filled with deionized water, (37° C.) and focused through an acoustic window of a 100 ml custom-made sample vessel. A pulser/receiver (model 5072 PR, Panametrics, Inc., Waltham, Mass.) was used to pulse the transducers at a pulse repetition frequency (PRF) of 100 Hz. The received signals were amplified to 40 dB and fed to the digital oscilloscope (Lecroy 9350A, Lecroy, Chestnut Ridge, N.Y.). The digitized data was stored and analyzed using LABVIEW™ software (National Instruments, Austin, Tex., USA). The bubbles were injected into the sample chamber using an automatic pipette, and stirred with a magnetic stirrer throughout the readings. The reference (PBS) is taken as an average of six values. Readings with buffer alone indicate that this method does not introduce unwanted air bubbles into the sample chamber. Enhancement and attenuation were calculated as a function of dose and time.

There are two curves which can be constructed from the acoustic set up. One curve is a dose response curve that demonstrates the echogenicity (dB of impinging sound that is reflected back to the transducer) of the bubbles. For each dose, a sample of the bubbles was added into 50 mL of PBS in the custom-made vessel then calculated and reported in the unit of μL of the bubbles per liter of PBS (μL/L). All of the dose response results are not cumulative. Another curve is a time response curve that demonstrates the testing of the stability of the bubbles overtime, under constant insonation. A dose on the linear rise of dose response must be chosen to conduct an accurate time response curve.

Particle Stabilization Theory Tested with Microbubbles Stabilized by Mixed SPAN® (Sorbitan Monostearate) and TWEEN® (Polyoxyethylene Sorbitan Monooleate)

Figure 10A:
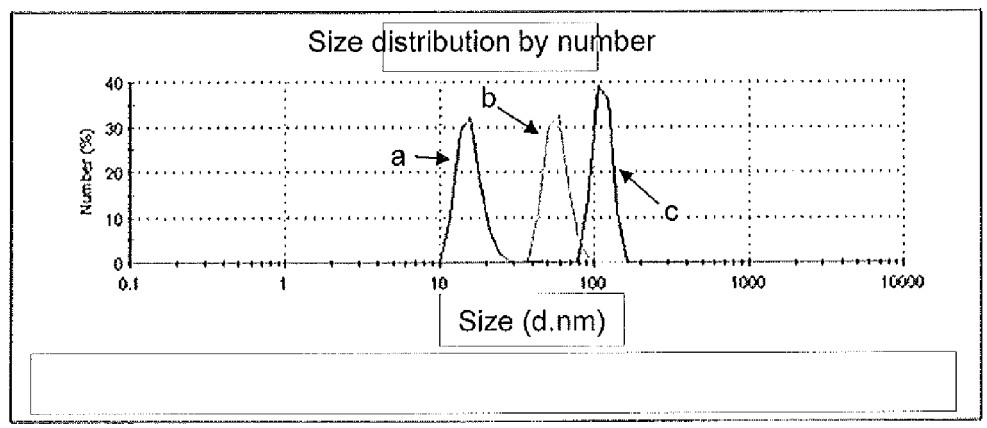
FIG. 10, consisting of panels A and B are a series of graphs depicting particle size distribution (FIG. 10A) of the mixture of 2 mM of SPAN® 60 (sorbitan monostearate) with 1 mM (curve a), 0.5 mM (curve b) and 0.1 mM (curve c) of TWEEN® (polyoxyethylene sorbitan monooleate) 80 in 50 ml of PBS and (FIG. 10B) the time response curve from in vitro ultrasound testing of microbubbles produced from the mixtures.
Figure 10B:
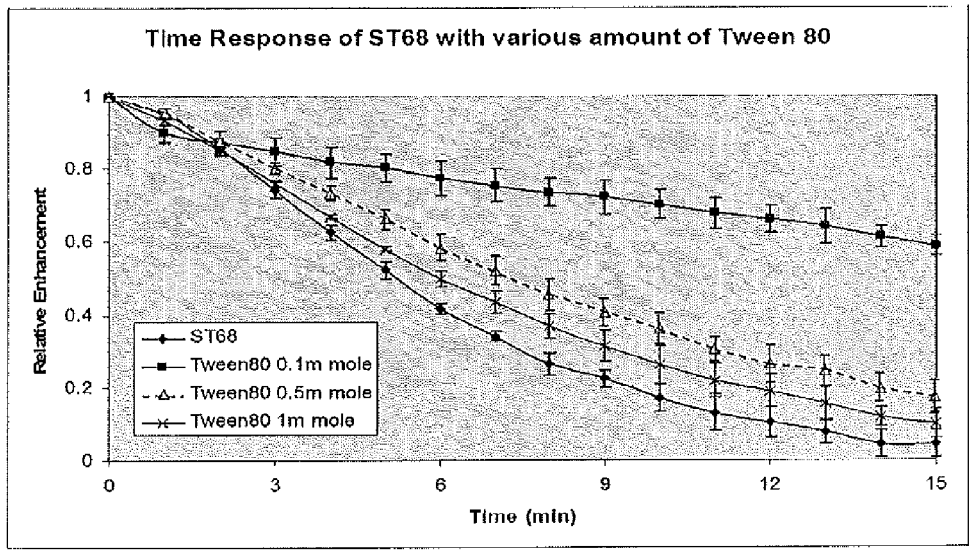

FIG. 10 shows size distribution and the time response curves of microbubbles stabilized by mixing 2 m mole of SPAN® 60 (sorbitan monostearate) with various concentration of TWEEN® 80 (polyoxyethylene sorbitan monooleate) (0.1, 0.5, and 1 m mole) in 50 ml of PBS with 1.5 g NaCl. All are above the CMC of TWEEN® 80 (polyoxyethylene sorbitan monooleate), which is 0.012 mM. From the size distribution results (FIG. 10A) one can see that the mean diameter of the particles decreases as the amount of TWEEN® 80 (polyoxyethylene sorbitan monooleate) increases relative to a constant amount of SPAN® 60 (sorbitan monostearate). When testing the bubbles produced from these mixtures in vitro, the bubbles were more stable as the diameter of the particles increased. The half-life of the microbubbles ($t_{1/2}$) is 6.02±0.48, 7.41±0.67, and 18.42±0.48 min. for 1, 0.5, and 0.1 m mole of TWEEN® 80 (polyoxyethylene sorbitan monooleate), respectively (FIG. 10B). These results agree with equation (1) that the bigger the particles, the more energy is needed to remove the particles from the interface. It should be note that the microbubbles produced from 2 m mole of SPAN® 60 (sorbitan monostearate) with 0.5 and 0.1 m mole of TWEEN® 80 (polyoxyethylene sorbitan monooleate) are statistically significantly more stable compared with standard ST68 (mixture of 3.44 m mole of SPAN® 60 (sorbitan monostearate) and 0.81 m mole of TWEEN® 80 (polyoxyethylene sorbitan monooleate), t1/2=5.20±0.20 min.), p=0.034 and 1.82×10-4, respectively. These results suggest that the behavior of microbubbles in in vitro testing can be explained by the particle stabilization theory.

Experimental Example 2

The Method for Fabricating Nano-Sized Contrast Agent

The Nanobubbles Produced from Higher Sonication Power

The mixture of nano- and micro-sized bubbles produced by the standard procedure can be separated by centrifugation (Oeffinger et al., 2004, Ultrasonic 42:343-347). One method to increase the proportion the nano-size bubbles is to change the sonication power during fabrication. Sonication at the power of 140 W instead of 110 W yield more nanobubbles, depending on the sonication time. For the sonication time of 90 and 120 sec., including 3 min, there are three distinct layers, which is the same as observed in the standard procedure to produce ST68. The size analysis of the collected middle layer is also in the range of standard microbubbles, which are in between 1-2 μm. It is different for the 30 and 60 sec. sonication time in that there is no distinct layer at 35 min. after washing step. If we assume that this lack of development of a distinct middle layer is due to the fact that there is a large population of very slowly rising nanobubbles, we can hasten the process and instead of waiting for these to rise and form a layer, we can discard the lower 20 ml of solution that contains unused surfactant, and collect the next 25 ml, which is the nano-rich layer. The mean diameter of the bubbles in this layer is around 787 nm. The echogenicity testing of this sample also shows that these "nanobubbles" gives almost the same as standard ST68 except that a higher dose is required to get the same result as standard ST68. From this result, it is possible that the amount of the nanobubbles can be increased by modifying some parameters and the protocol to collect the bubble of the current procedure to get the nanobubbles.

Nanobubbles Produced by Changing Surfactant Components

Another potential method to produce a larger proportion of nanobubbles is to change the surfactant composition. The standard procedure was carried out except for the washing and collecting step. Because there was no distinct layer after one hour after the first wash with 50 ml PBS, the lower 25 ml was discarded and then the next 50-75 ml of the mixture was transfer to a separation funnel B while the remaining mixture was left in funnel A. Both separation funnels A and B are then carried through the washing and separation step in parallel, being washed with 50 ml PBS twice. The Funnel A produced three distinct layers after 35 min. standing after both washing step. The middle layer was collected in the same procedure as for standard ST68 and these bubbles are called SE61. SE61 had the same mean diameter in the range of standard ST68, which is in between 1-2 μm. For the newly transfer funnel B, each washing step was left to separate for one hour. At the end of the waiting period, the lower 20 ml of solution was discarded from the separating funnel. The mixtures was collected after the last discard and called nSE61. These nanobubbles have mean diameter of 337.67±19.77 nm.

The normalized time response of SE61 and nSE61 compared with standard ST68 show that the differences among all three agents are statistically significant (p=0.0485 for ST68 and SE61 and p=3.72×10-4 for ST68 and nSE61). The SE61 (t1/2=10.18±1.77 min.) is more stable than the standard ST68, which will be a benefit for using it as a contrast agent. However, nSE61 (t1/2=1.75±0.24 min.) is considerably less stable than standard ST68. A susceptibility to ultrasound of the nano agent might be a benefit for the drug release when using the nanobubbles as a drug carrier.

Experimental Example 3

Drug Delivery

The agent ST68 was chosen for the preliminary study of Nile Red loaded microbubbles, since this agent is well characterized. Nile Red was added into the solution after the sterilization step and then heated until the solution boiled for 3-5 min. At this point, the solution color changed from milky white to pink or red depending on the amount of Nile Red that was added. This is due to Nile Red becoming dissolve into micelles, and fluorescing in the nonpolar environment of the micelle. The solution was then left to cool down to room temperature. Microbubbles were then made by the usual protocol (sonicate at 110 W for 3 min.).

The qualitative analysis of Nile Red intercalated to the bubbles can be tested by the fluorescent property of Nile Red. It is strongly quenched in aqueous media but fluoresces depending on the polarity of its environment. As Nile Red is intercalated into the hydrophobic shell of the bubbles, under fluorescent microscopy, the shell of the bubbles fluoresce as can be seen.

The echogenicity of Nile Red loaded microbubbles was tested. It was found that both the dose and the time response of the Nile Red loaded bubbles are not statistically significantly different (p<0.05) from regular ST68.

Micelles of Low Ratio SPAN® 60 (Sorbitan Monostearate) to TWEEN® 80 (Polyoxyethylene Sorbitan Monooleate) for Drug Delivery Another approach to nanocarriers for poorly water-soluble drug delivery is to use polymeric micelles. The hydrophobic drugs can be solubilized in their hydrophobic inner cores. This study of using a mixed surfactant system for a contrast agent also makes possible a study of the mixed micelles of these surfactants as drug carriers. At the ratio of 20:80, the mixed micelle of SPAN® 60 (sorbitan monostearate) and TWEEN® 80 (polyoxyethylene sorbitan monooleate) can be formed without suspended particles and the mean size of these micelles is around 9.9 nm.

The qualitative analysis for solubilized Nile Red was analyzed by HPLC with acetonitrile as mobile phase with UV detector at $\lambda_{max}$ 538 nm. This wavelength was found to be correct for the maximum absorbance of Nile Red dissolved in acetonitrile using the Plate Reader. A calibration curve of Nile Red in acetonitrile analyzed by HPLC was established ($R^2$=0.9999). It was discovered that SPAN® (sorbitan monostearate) and TWEEN® (polyoxyethylene sorbitan monooleate) interfered with the analysis of Nile Red. As a modification, petroleum ether was first used to extract Nile Red from the mixture by mixing 5 mL of the mixture with 5 mL of Petroleum Ether. This mixture was shaken for 15 sec., and then placed in the centrifuge with a setting of 9000 rpm (4500 g) for 30 min. After the centrifugation, 2 mL of the top layer of petroleum ether was pipetted into a glass vial, and the petroleum ether was allowed to evaporate under the fume hood. Two mL of acetonitrile was added to dissolve Nile Red. To make sure that Nile Red completely dissolved, the vial was sealed and shaken for 48 hr before being analyzed by HPLC. From the results, one can see that in the solution of total concentration surfactant of 85.1 mM, Nile Red can be solubilized in the mixed micelles at the maximum concentration of 47 mg of Nile Red in one liter of solution.

The echogenicity of the mixtures of the bubbles and the micelles is around 25 dB at a dose of 50 µl/L and $t_{1/2}$ around 5 min. This test shows that the equilibrium of the bubbles system is not altered by mixing in the micelles, at least in 30 minutes, and makes possible the mixing system for drug delivery.

Experimental Example 4

Freeze-Drying Enhances Storage and Stability of the UCA

To assess lyoprotection, four candidate saccharides were tested as lyoprotectants: glucose, trehelose, sucrose and mannitol.

Aliquots of 2 mL undiluted ST68 are placed in 15 mL lyophilization vials (West Pharmaceutical Services, Lionville, Pa.) in a 1:1 volume ratio of 200 mM (1.8 w/v %) sugar lyoprotectant dissolved in 18.6 MS2 cm deionized (DI) water. Samples were frozen in liquid nitrogen while FLUO-RTEK® lyophilization stoppers (West Pharmaceutical Services) were placed on the vials to the first groove. The cryoprotected ST68 was dried on a previously chilled (−80° C.) shelf for 20 to 24 hours using a VIRTIS® benchtop freeze-dryer (Gardiner, N.Y.) at pressures below 200 par. Prior to venting, a piston was lowered thus sealing the stoppers on the vials. After the vials were shaken and tapped on the table to disperse the particles from their freeze-dried cake, octafluoropropane gas was introduced, via needle, into the vials through the stopper septum at a flow rate of 6 mL/min for the first 5 to 10 seconds, then 4 mL/min for 3½ minutes to insure the vials were filled. Filling time was adjusted based on the volume (15 mL) of the lyophilization vials. PARAFILM® film was wrapped around the stopper/vial seal to prevent gas diffusion. Before use, the freeze-dried ST68 was reconstituted with 1 mL DI water and 1 mL phosphate buffered saline (PBS) both at 4° C. by hand agitating.

Effect of Choice of Lyoprotectant on UCA Size

For all lyoprotectants, bubble size remained constant at 3±0.15 µm. All samples were significantly less than 6 µm, ensuring they would be able to transverse the pulmonary capillary bed.

In Vitro Acoustic Performance

Both glucose and trehalose provided statistically greater in vitro enhancement (p<0.001) than that of the reconstituted ST68 control (freeze-dried without the addition of any lyoprotectant), both giving a peak enhancement of about 23 dB, comparable to the enhancement of freshly prepared ST68. Samples lyophilized in the presence of sucrose and mannitol provided a peak enhancement of about 18 and 19 dB, respectively, but were not statistically greater than the control, which yielded about a 17.5 dB peak enhancement. For all sugar controls (freeze-dried dissolved sugar in PBS without the addition of ST68), a maximum enhancement of about 2 dB was recorded signifying that the lyoprotectant itself did not cause the increase in enhancement over that of the ST68 samples.

A study of stability was also completed for all lyoprotectants at room temperature (20° C.) and body temperature (37° C.) for comparison. At 37° C., there was no statistical different between the half-lives of any reconstituted ST68 with or without lyoprotectants. However, after the first rapid loss of echogenicity, the samples preserved with glucose retained the highest residual activity (20% at 15 minutes compared to ~5% for freshly prepared agent).

However, glucose provided longer stability at 20° C. over the ST68 control (p<0.01) and all other lyoprotectants (p<0.05 over sucrose and <0.01 over all others). Reconstituted ST68 even at 37° C. retains measurable echogenicity for over 10 minutes in vitro.

Effects of Freeze-Drying and Lyoprotectants on Reconstitution

Upon reconstitution, mannitol, sucrose, and control samples were unable to be completely re-suspended, leaving behind visually large particulates which might prove dangerous if injected into the body. These larger particles evaded detection in the size analysis due to their buoyancy.

Glucose Concentration Optimization

A range of glucose concentrations, from 20 mM to 400 mM or 0.2 to 3.6 w/v %, was tested for optimization. While not statistically significant, 200 mM of glucose (ST68G-200) provided a 4 dB greater enhancement over the other concentrations, providing a peak enhancement of about 23 dB. However, the half-life at 37° C. of all glucose cryoprotected agents remained constant at an average of 3+0.3 minutes signifying the concentration of glucose did not significantly affect the ST68 stability.

In Vivo Study

The in vivo dose response experiments of ST68G-200 were modeled after previous studies (Forsberg et al., 1996, supra; Wheatley et al., 2006, supra) of freshly prepared ST68 for direct comparison. An average peak enhancement of about 23 to about 25 dB were recorded for the freshly prepared ST68. The freeze-dried agent ST68G 200 was chosen for this study based on the results outlined above, and provided a peak enhancement of about 21 dB, being on average 3 dB under that of the freshly prepared ST68.

Pulse inversion harmonic imaging (5 MHz) of a New Zealand white rabbit kidney pre and post injection of ST68G-200 was performed. The vasculature and parenchyma boundaries of the kidney are clearly visible after injection of 0.1 mL/kg contrast.

Microscope Imaging

To show the difference between ST68g-200 and ST68 without lyoprotectant, S.E.M. images were taken of both. Protected bubbles can be seen in with lyoprotectant present while without addition of a lyoprotectant, bubbles are not present.

Experimental Examples 5-11

Experimental Examples 5-11 are directed to describing and characterizing in more detail the lyoprotection of the UCA studied in Experimental Example 4. The materials and methods for Experimental Examples 5-11 are now described.

Materials

SPAN® 60 (sorbitan monostearate), TWEEN® 80 (polyoxyethylene sorbitan monooleate), potassium chloride, sucrose, D-glucose anhydrous, D-mannitol, D-trehalose dihydrate, potassium phosphate monobasic, sodium chloride, and sodium phosphate dibasic were all purchased from Sigma-Aldrich (St. Louis, Mo.). Octafluropropane (99% min) was purchased from American Gas Group (Toledo, Ohio).

Sample Preparation

ST68 was manufactured using a method developed in our laboratory (Wheatley et al., 1994; Wheatley and Singhal 1995; Wheatley et. al 2006). Aliquots of 2 ml of non3 diluted ST68, were placed in 15 ml lyophilization vials (West Pharmaceutical Services, Lionville, Pa.) and diluted with 2 ml of a solution of selected sugar lyoprotectant dissolved in DI water. Samples were flash frozen in liquid nitrogen (shown to prevent sample and solvent separation (Costantino and Pikal 2004) and improve the redispersion of nanoparticles (Lee et al., 2009) with FLUOROTEK® 7 lyophilization stoppers (West Pharmaceutical Services) placed on the vials to the first groove as exemplified by Jennings (1999). The lyoprotected ST68 was dried on a previously chilled (initially to −80° C.) shelf for 18 to 20 hours using a VIRTIS° benchtop freeze-dryer (Gardiner, N.Y.) at pressures below 300 par and a condenser temperature of −76° C. Prior to venting, a piston was lowered thus sealing the stoppers on the vials. To measure the temperature profile of the samples, a thermocouple was frozen within the center of the matrix prior to lyophilization. The temperature of the frozen matrix was recorded every 10 minutes on a remote 4 Channel Datalogger Thermometer (Sper Scientific LTD, Scottsdale, Ariz.) for the duration of the freeze-drying process.

After the ST68 samples were lyophilized, octafluoropropane gas was introduced via a needle into the vials through the stopper septum at a flow rate of 50 ml/min for the first 5 to 10 seconds then 20 ml/min for the next minute to insure the vials were filled. Finally, PARAFILM® film was wrapped around the stopper/vial seal to prevent gas diffusion. Before use, the freeze-dried ST68 was reconstituted by hand agitation with 2 ml DI water and 2 ml phosphate buffered saline (PBS), both at 4° C., yielding a 1:1 dilution facto compared to the original non-diluted sample.

Residual Water Content

Freeze-dried samples of ST68 in lyophilization vials were unstoppered and weighed. Each vial was then placed within an Imperial III incubator (Lab-Line Instruments Inc., Melrose Park, Ill.) set to 60° C. for 24 hours and weighed again. This procedure was repeated until the weight of the samples remained constant indicating that all residual water had been removed. The water content was calculated as a percentage of initial weight.

Size Characterization

All size measurements were carried out using a ZETA-SIZER® NANO ZS™ (Malvern Inst., Worcestershire, UK). Twenty-five pi of agent was dispersed into 975 μl of PBS and gently inverted to ensure thorough mixing. For each sample, three measurements (z13 average diameter which was found to be more consistent in measuring ST68 size than number or size average) were taken and averaged together.

Microscope Imaging

Polarized Light Microscopy (PLM) images of ST68 samples were taken of individual drops of ST68 with each excipient. These samples were previously placed onto a glass slide and frozen in a −80° C. freezer before being lyophilized overnight. PLM images were taken at 20× with an OLYMPUS® BX50 model U-SDO (Tokyo, Japan) using PIXELINK® Capture OEM 2005 software (Ottawa, ON, Canada).

Samples of ST68G-100 (100 mM glucose stabilized freeze-dried ST68) and ST68 control (freeze-dried without lyoprotectant) were prepared on an aluminum specimen mount, previously covered with a 12 mm non 1-conductive adhesive tab, having excess sample blown off with pressurized air. Samples were then carbon coated for 8 seconds using a CRESSINGTON™ 208 bench-top carbon evaporator (Watford, England). Images were taken with a ZEISS® SUPRA™ 50 (Cambridge, Cambridgeshire, UK) scanning electron microscope (S.E.M.) with Oxford Energy Dispersive Microanalysis (EDS) (Abingdon, Oxfordshire, UK) set to 3.5 kV and with an aperture of 4 mm.

In Vitro Acoustic Setup

An acrylic sampling container holding 50 ml of 37° C. PBS, housing an acoustic viewing window of 3×3 cm, was placed within a larger acrylic tank holding 20 gallons of 37° C. DI water to be used for acoustic testing of the samples, as previously described (Basude et al., 2000). The contents of the sampling container were continuously stirred with a magnetic stirrer between 200 and 400 rpm. A PANAMETRICS® (Waltham, Mass.) 5 MHz transducer with a 12.7 mm diameter, −6 dB bandwidth of 91%, and focal length of 50.8 mm was focused through the sampling window. Acoustic pressure amplitudes were generated with a PANAMETRICS® pulse/receiver (5072 PR) at a pulse repetition frequency (PRF) equal to 100 Hz. Using a 0.5 mm polyvinylidene fluoride needle hydrophone (Precision Acoustics, Dorset, UK), peak positive and negative pressures were measured at 0.69 and 0.45 MPa, respectively. Received signals were amplified 40 dB and read using a digital oscilloscope (LECROY® 9350A, LeCroy Corporation, Chestnut Ridge, N.Y.). LABVIEW™ 7.1 express (National Instruments, Austin, Tex.) was utilized to process the data.

In Vitro Dose and Time Response

Quantities of test samples of ST68 were measured by pipette (GILSON PIPETMAN®, Middleton, Wis.) and dispersed into the sampling container. A cumulated dose curve (expedient for discerning comparisons between lyoprotectants) was generated by pipetting increments of agent into the sample chamber while measuring the acoustic response. The curve was used to determine the dose at which maximum reflection was achieved and to assess differences between samples prepared with various lyoprotectants. Shadowing occurred when the concentration of bubbles was high, thus causing a total reflection of the US signal (Bogdahn et al., 2001, Transcranial color-coded duplex sonography (TCCS). In: Dunitz, M. (Ed.) Ultrasound Contrast Agents: Basic principles and clinical applications. Martin Dunitz Ltd., London, UK., pp. 253-65). To examine the stability of the UCA while being exposed to an ultrasound beam, samples on the rise of the dose response curve (100 µl/l for reconstituted freeze-dried samples and 30 µl/l for the native agent) were insonated over a 15 minute period with readings taken every minute, after a 10 second delay to allow for sample mixing. The chosen volumes gave similar concentrations of microbubbles (2.5 to $3.0 \times 10^9$ microbubbles per milliliter as measured by a hemocytometer) and were selected to prevent anomalous high stability readings that would be obtained by recording unchanged enhancement from degrading bubbles in an over-saturated system. Data was normalized by the initial dB value to allow for inter sample comparison. Half-life data was extracted from the response of the agents over time by fitting a line to the section of the curve which passed through 50% of maximum enhancement. For all, a native ST68 and a freeze-dried (not lyoprotected) control were used for comparison.

In Vivo Acoustic Testing

Dose response curves were generated in three 3 kg New Zealand white rabbits with ST68G-100. Each rabbit was sedated with 35 mg/kg ketamine and 3.5 mg/kg xylazine. Increasing volumes, from 0.005, 0.01, 0.05, 0.1, to 0.15 ml/kg were injected through an angiography catheter inserted into the left ear vein, followed by a flush of 5 ml sterile saline. Roughly 5 to 10 minutes passed between each dose to ensure total removal of the agent and a return to baseline values. A SONIX® RP scanner (Ultrasonix Medical Corp., Richmond, BC, Canada) recorded all data received by the L14-5 linear array set to 5 MHz with a PRF of 6.7 kHz and a gain of 44% in pulse Doppler mode, having been focused on the mid abdominal aorta. Pulse inversion harmonic imaging (PIHI), with a power of −8 dB and a PRF of 1 kHz, was used to image the kidney with a dose of 0.1 ml/kg. These studies were carried out under the guidance of a veterinarian and all protocols were approved by Jefferson University's Animal Care and Use Committee. A similar dose curve was previously generated with native and nano ST68 (Forsberg et al., 1996, supra; Wheatley et al., 2006, supra).

Statistical Analysis

All data is presented as mean+SEM (standard error about the mean) with all experiments repeated at least 3 times (n=3). For all data, statistical significance was determined using a one-way ANOVA with a Newman-Keuls post test assuming normal distribution and focusing on comparisons with controls. All testing was performed using PRISM™ 3.0 (GraphPad, San Diego, Calif.) with a probability value cut off of 0.05 chosen to determine statistical significance.

The results for Experimental Examples 5-11 are now presented.

Experimental Example 5

Effect of Each Lyoprotectant on the UCA

For all four candidate lyoprotectants, bubble size remained constant with an average of 3+0.2 µm with no statistical difference calculated between samples (p>0.05). These results are larger than previously reported (Basude et al., 2000, supra). All samples were significantly less than 8 µm, ensuring they would be able to transverse the pulmonary capillary bed (Bouakaz et al., 2007, Ultrasound Med. Biol., 33, 187-96).

Upon visual inspection, it was apparent that large particles remained after reconstitution for the mannitol and sucrose samples; this also occurred with non-lyoprotected ST68 control samples. Since these large particles were buoyant, they rapidly rose to the top of the cuvette and thus eluded ZETASIZER® measurements, which are based on Brownian motion of particles in the target area. The observation that the glucose-lyoprotected sample did not result in large particles is unexpected. Literature suggests that the particles freeze-dried in the present of glucose would also have reconstitution problems (Abdelwahed et al., 2006a, supra).

Figure 12:
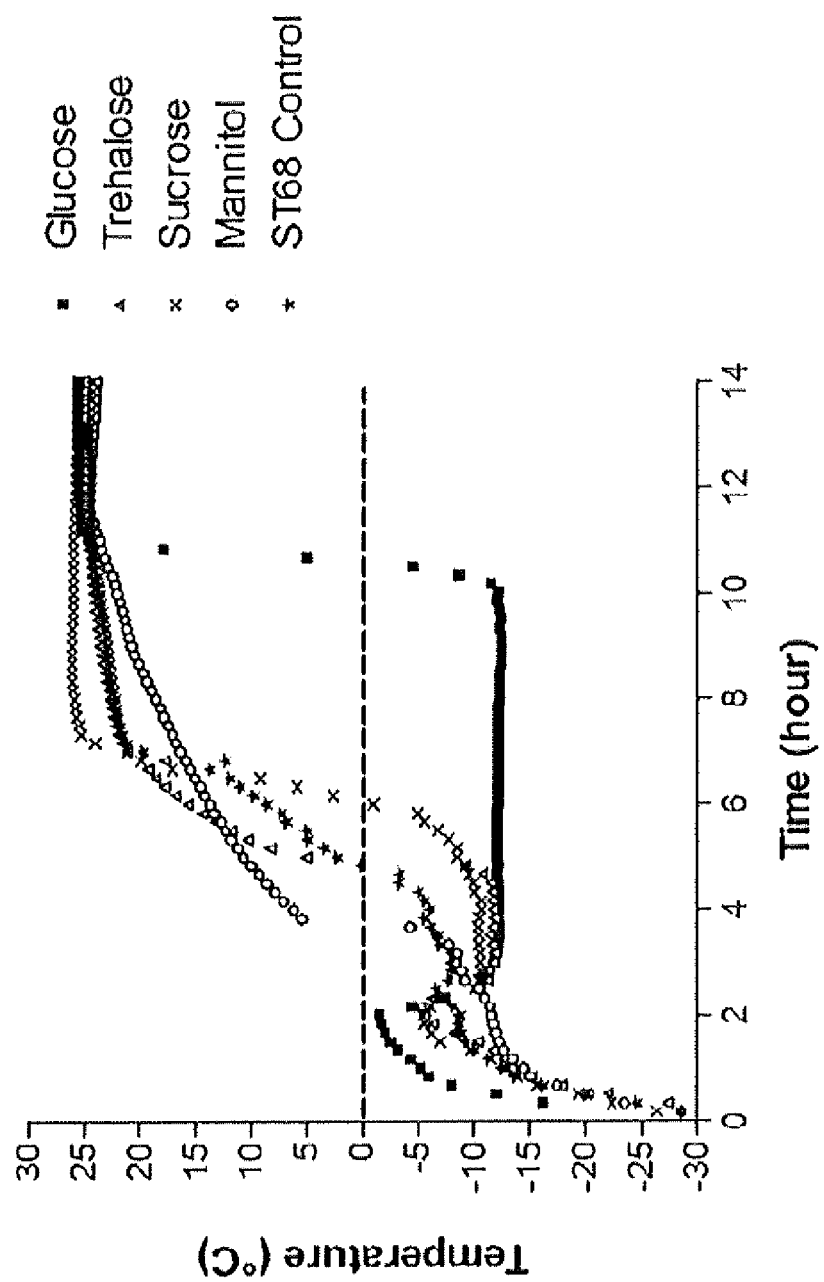
FIG. 12 depicts a graph of recorded temperature readings of lyoprotected (100 mM) and control ST68 samples during freeze-drying. Glucose addition maintained the sample at a constant temperature of −12° C. longer (7 hours) than other excipients: 1 to 2 hours for trehalose or sucrose addition, and mannitol addition having a steadily rising temperature profile.

During lyophilization, the thermocouples embedded in sample vials indicated that glucose was able to keep the sample at a temperature of −12° C. (zero slope, linear portion of the temperature/time curve; FIG. 12) for the longest period of time (7 hours). Trehalose and sucrose maintained this temperature for only 2 hours, while mannitol merely passed through, exhibiting a constantly rising temperature profile. All samples, aside from mannitol-protected ST68, had an initial rise in temperature to the 2 hour mark followed by a cooling to the −12° C. steady state sublimation temperature.

After lyophilization, all of the samples had between 2 and 6% residual water content (Table 2), with no statistical differences measured (p>0.05). Trehalose samples had the lowest (2.2+0.2%) while glucose and control samples were around 5%. Water content alone did not affect the overall echogenicity or stability of the sample.

TABLE 2

| Excipient | Water Content (%) |
| --- | --- |
| Glucose | 5.0 ± 0.2 |
| Trehalose | 2.2 ± 0.2 |
| Sucrose | 4.2 ± 1.3 |
| Mannitol | 4.1 ± 0.1 |
| ST68 (control; no saccharide) | 5.2 ± 0.8 |

Experimental Example 6

In Vitro Acoustic Performance

Figure 13:
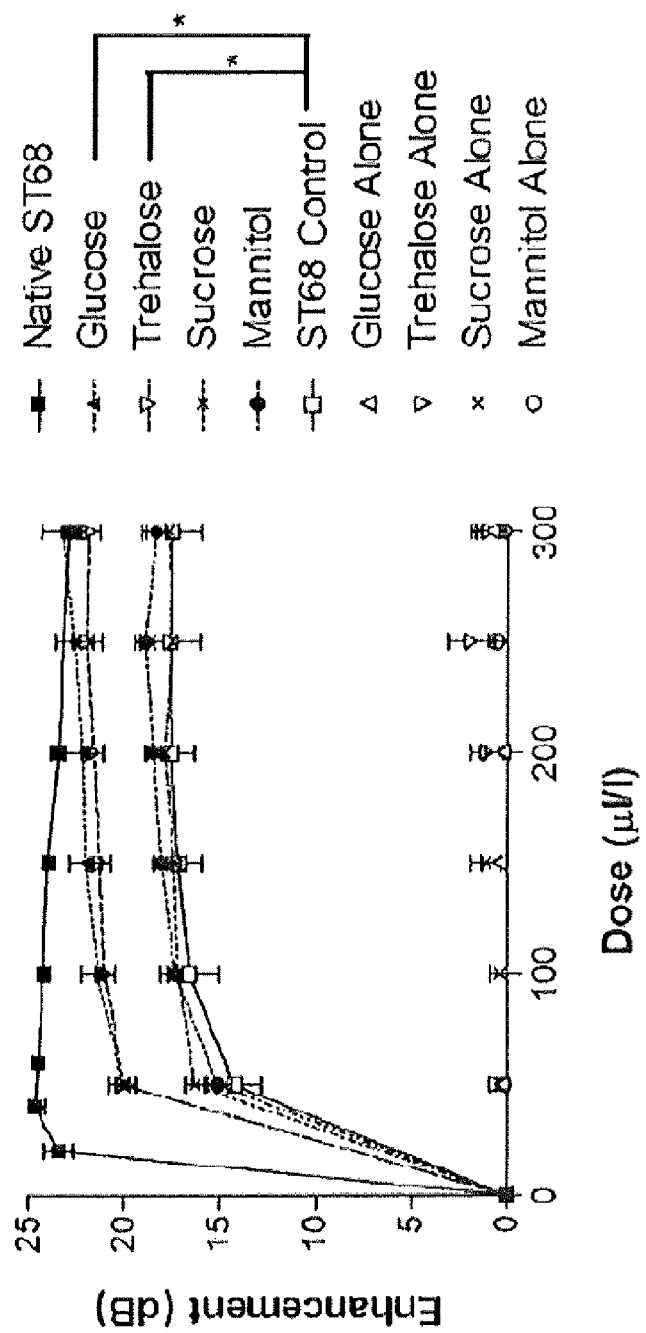
FIG. 13 depicts a dose response curve for lyophilized ST68 in a variety of 100 mM candidate lyoprotectant solutions. All sugar controls (e.g., glucose alone) are dissolved in PBS, lyophilized, and PFC gas introduced but do not contain any agent. Glucose and trehalose were significantly greater than the control, the sucrose and the mannitol by the same degree (*p<0.001, error bars=SEAM, f=5 MHz, 684 kPa, PRF=100 Hz).

At 100 mM (Huang et al., 2002, supra), both glucose and trehalose provided statistically greater in vitro enhancement (p<0.001) than that of the reconstituted sucrose, mannitol, and the ST68 control (freeze-dried without the addition of lyoprotectant) (FIG. 13). A peak enhancement of 23.2±1.2 dB and 21.9±0.7 dB were measured for glucose and trehalose, respectively, both being statistically equivalent (p>0.5) to the 24.5±0.2 dB enhancement of native ST68. Samples lyophilized in the presence of sucrose and mannitol provided a peak enhancement of 17.9±0.1 dB and 18.9±0.5 dB, respectively, but were not statistically greater than the control, which yielded a 17.6±1.6 dB peak enhancement (p>0.05). For all sugar controls (freeze-dried dissolved sugar in PBS without the addition of ST68), an average enhancement of 0.4±0.1 dB was recorded, signifying that the lyoprotectant itself did not have any inherent echogenic properties.

Although all the tested lyoprotectants resulted in lyophilized material that reconstituted to give over 15 dB of enhancement, glucose and trehalose provided the best protection resulting in a 5 dB increase over the others. It is surprising that both glucose and trehalose provided the best protection. It has been reported the protective effects of saccharides are proportional to their glass transition temperatures ($T_g$; Hua et al., 2003, supra). Experimental and calculated glass transition temperatures ($T_g$) of some of the pure sugars of interest have been reported as trehalose (107° C.), sucrose (60° C.), glucose (23° C.) (Simperler et al., 2006, J. Phys. Chem. B, 110, 19678-84), while mannitol is reported at 11° C. (Yu et al., 1998, J. Pharm. Sci., 87, 774-7). The studies in Hua exhibited that the retention rates for reconstituted freeze-dried liposomal contents followed the same trend as the $T_g$, indicating that the best protection was from trehalose and the worst from glucose. Therefore, the equal protective effects of glucose and trehalose demonstrated here are unexpected and suggests that there is more involved in stabilizing UCA than with liposomes.

Figure 14:
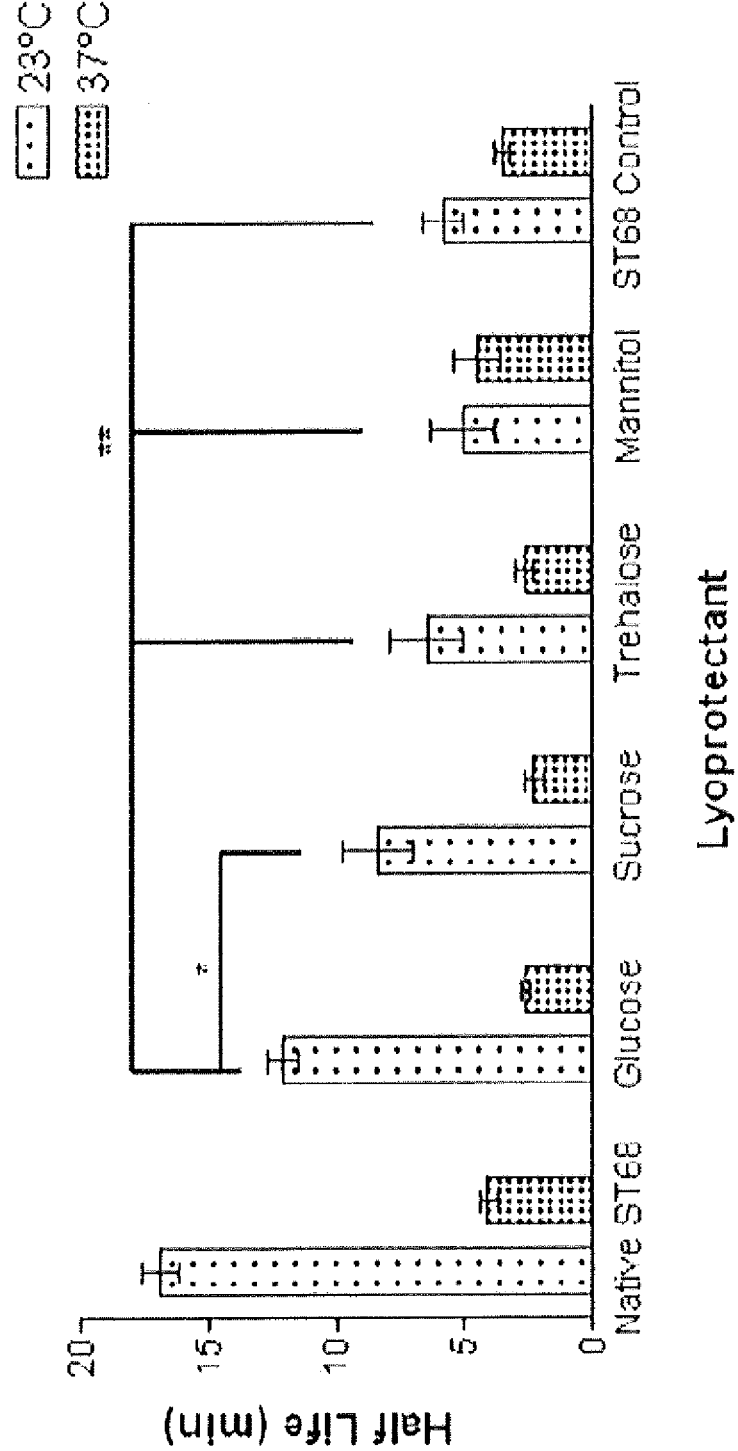
FIG. 14 depicts a bar graph of the half-life of lyophilized ST68 in a variety of 100 mM candidate lyoprotectant solutions tested at room (23° C.) and body (37° C.) temperature. ANOVA testing revealed ST68 with glucose at room temperature to be the only lyoprotected agent statistically greater than that of the ST68 control and all other lyoprotectants (*p<0.05, **p<0.01). (f=5 MHz, 684 kPa, PRF=100 Hz).
Figure 15A:
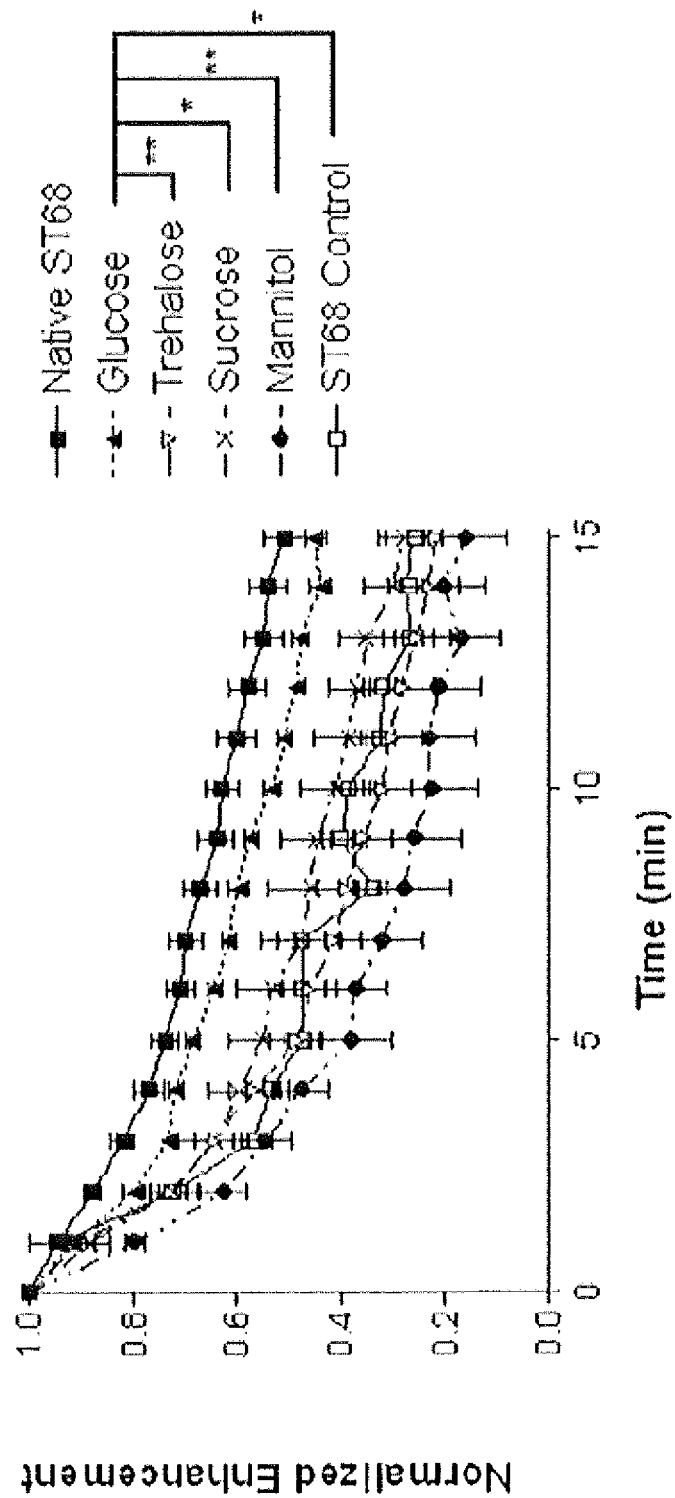
FIG. 15, consisting of panels A and B are a series of graphs depicting normalized time response of lyophilized ST68 in 100 mM lyoprotectant solutions tested at 23° C.

A study of stability (FIG. 14) was completed for all lyoprotected samples at room temperature (23° C.) and body temperature (37° C.). At 23° C. glucose provided longer stability (12.1±0.6 min.) over the ST68 control (5.8±0.8 min., p<0.01) and all other lyoprotectants (p<0.05 over sucrose and <0.01 over rest). After 15 minutes, samples preserved with glucose retained the highest residual activity (45%; 7±0.4 dB) over all the other lyoprotected samples (p<0.05 for sucrose and ST68 control, p<0.01 for trehalose and mannitol) and did not statistically differ from native ST68 (55%; 11.7±0.9 dB) over the duration (FIG. 15A). At 37° C., there were no statistical differences (p>0.05) between the half-lives of any reconstituted lyoprotected ST68 when compared to the naked reconstituted control, yielding an average half-life of 3.1±0.5 minutes (FIG. 14) and sustaining measurable echogenicity for over 10 minutes (FIG. 15B).

Experimental Example 7

Polarized Light Microscopy

Figures 16A, 16B:
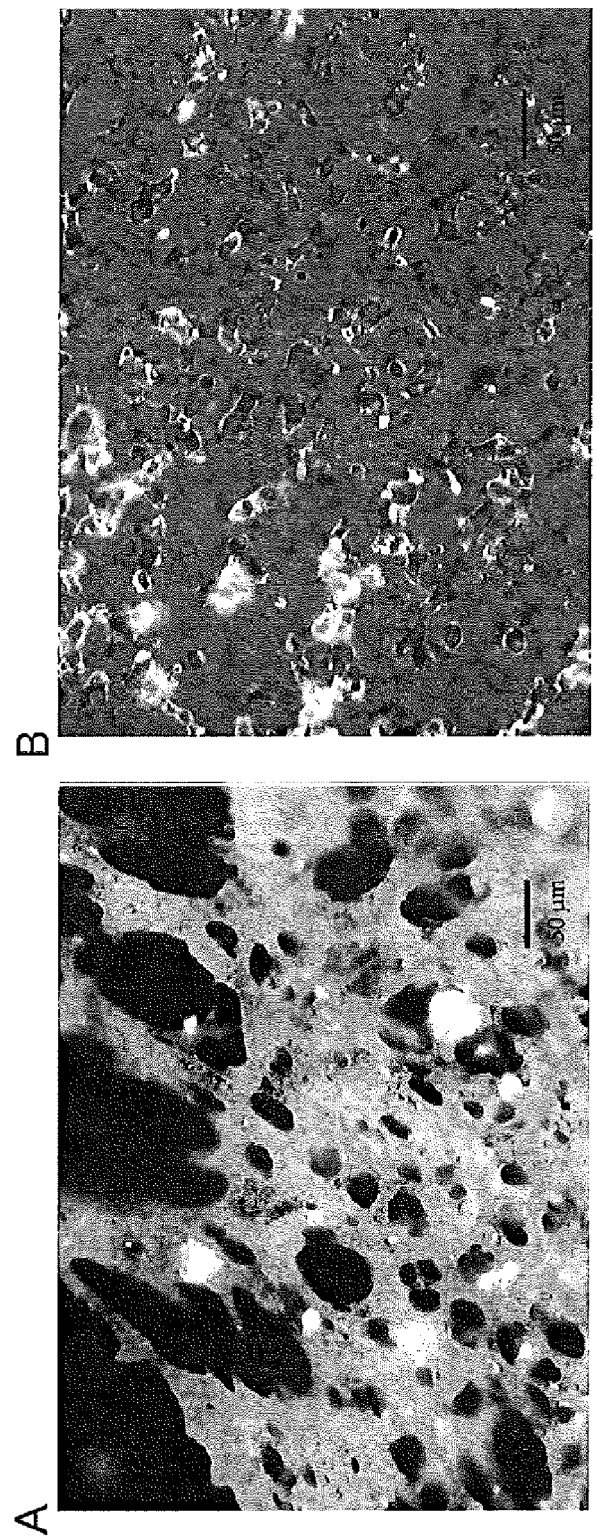
FIG. 16, consisting of panels A-E are a series of OLYMPUS® BX50 PLM images taken at 20× of lyophilized samples of ST68 with and without candidate lyoprotectant excipients (100 mM). Mannitol (FIG. 16, panel D) shows a crystalline structure while the others excipients form glassy matrices. Control ST68 samples (FIG. 16, panel E) contained no evidence of either an amorphous glassy matrix or crystallization, being diluted 1:1 with PBS instead of a sugar solution. Visually, glucose protected ST68 (FIG. 16, panel A) seems to form the most intact glassy matrix with trehalose (FIG. 16, panel B) and sucrose (FIG. 16, panel C) have glassy spindles.
Figures 16C, 16D:
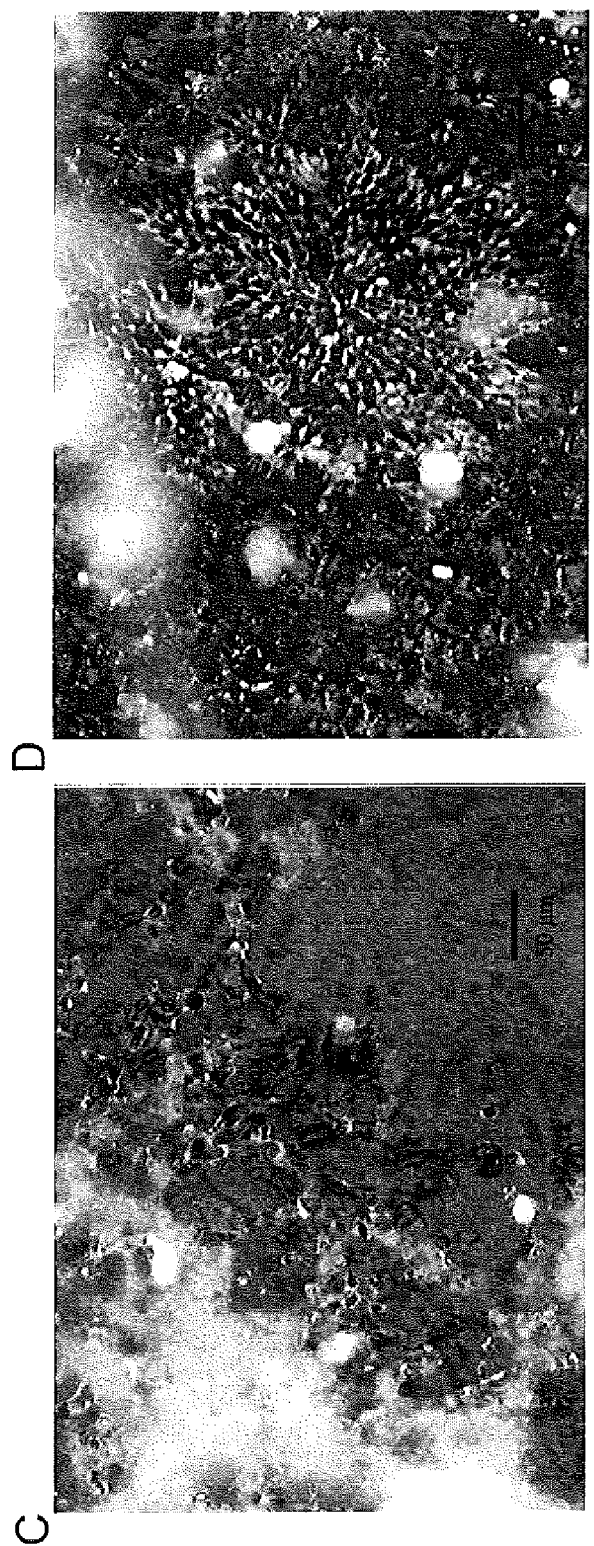
Figure 16E:
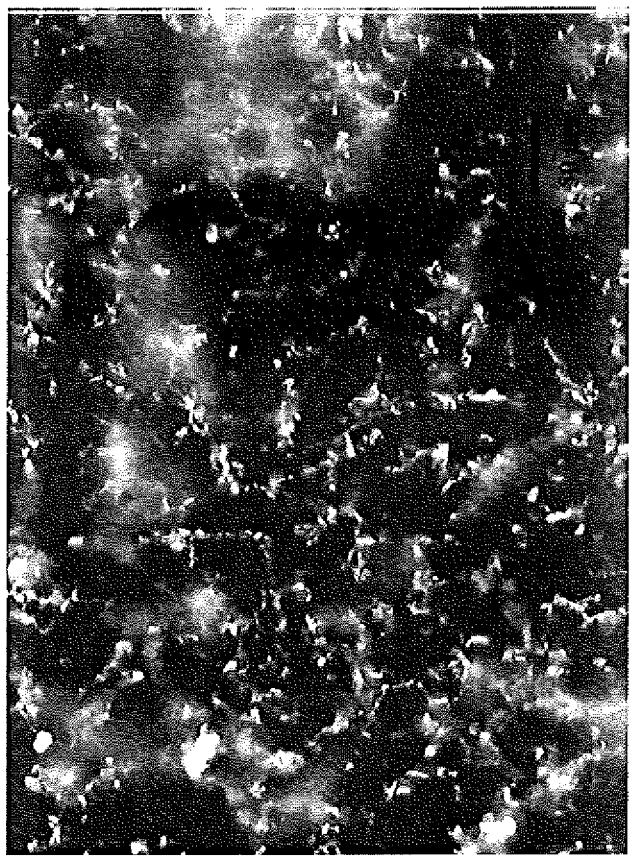

PLM images were taken to better describe the apparent mechanism of stabilization of the different sugars. The images illustrate that mannitol (FIG. 16D) is the only excipient that crystallized while glucose (FIG. 15A), trehalose (FIG. 15B) and sucrose (FIG. 15C) formed amorphous glassy matrices. ST68 control, without any lyoprotectant (FIG. 15E) is amorphous as well, but does not show any presence of a glassy matrix.

Experimental Example 8

Glucose Concentration Optimization

Figure 17:
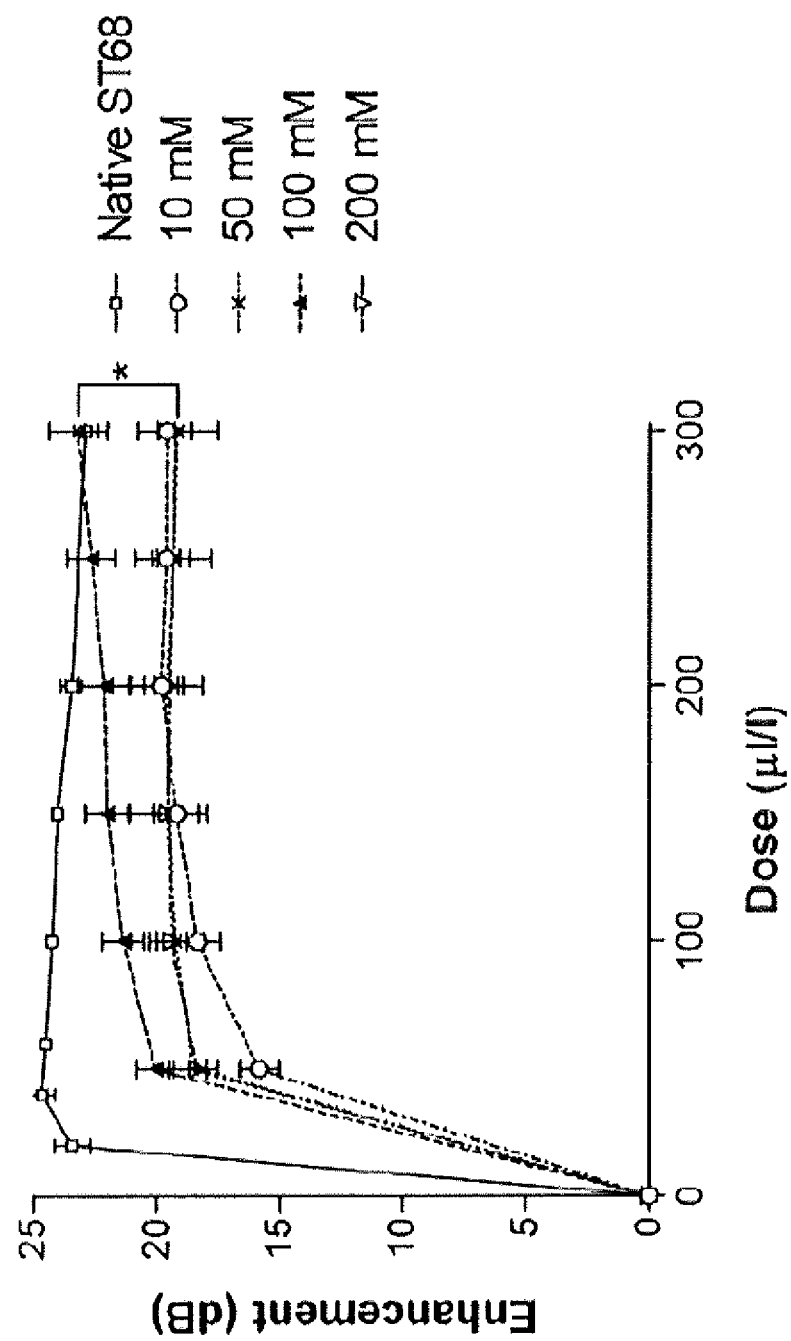
FIG. 17 depicts a dose response curve of lyophilized ST68 in various glucose concentrations. No statistical differences measured (p>0.05). (f=5 MHz, 684 kPa, PRF=100 Hz).
Figure 18:
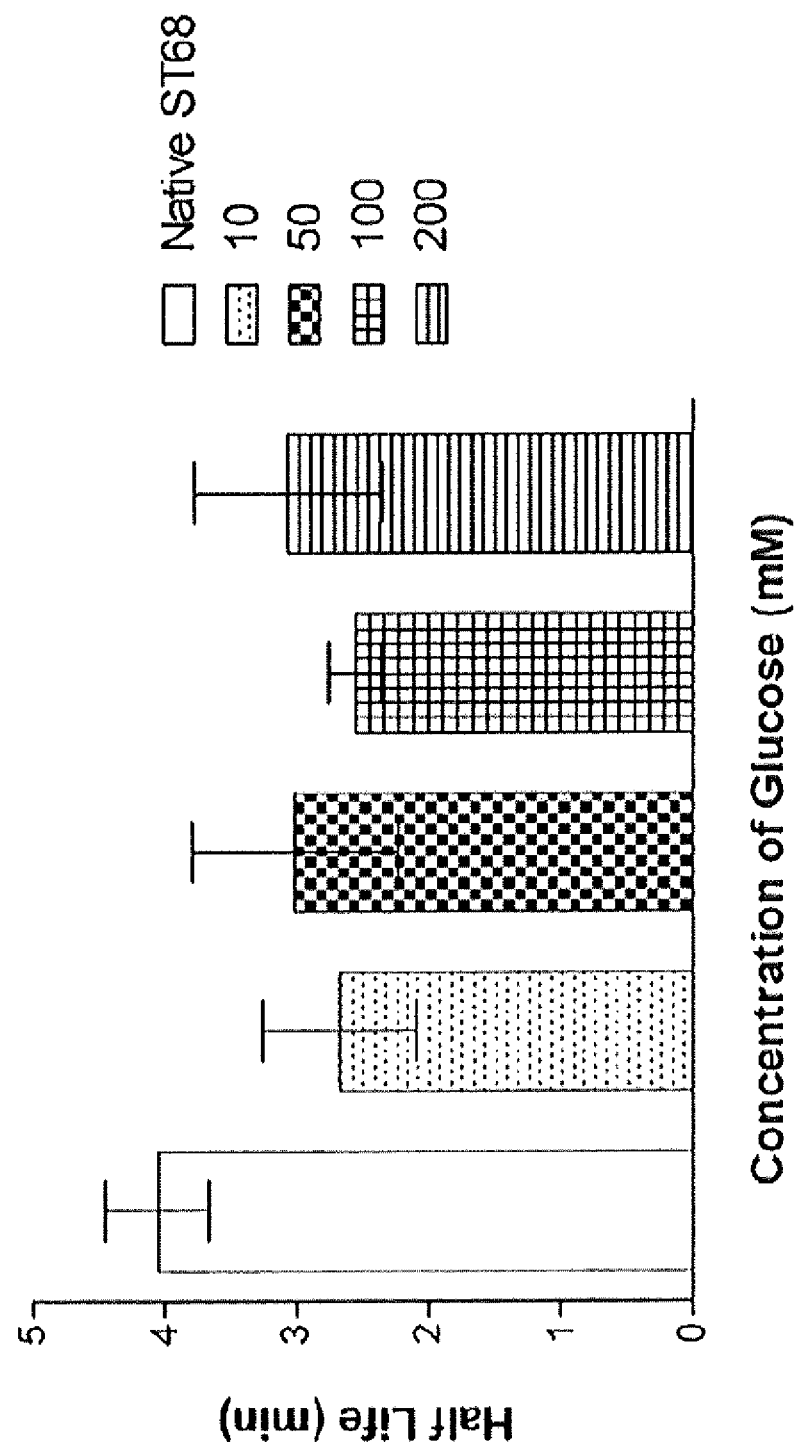
FIG. 18 depicts a bar graph of half-life data of lyophilized ST68 in various glucose concentrations. No differences are statistically significant (p>0.05). (f=5 MHz, 684 kPa, PRF=100 Hz).

A range of final glucose concentrations, from 10 mM to 200 mM or 0.2 to 3.6% w/v, was tested for optimization. This range is consistent with concentrations used for freeze-drying in literature (Jeong et al., 2005, J. Microencap., 22, 593-601). While not statistically significant (p>0.05), 100 mM of glucose-protected samples (ST68G-100), 1.8% w/v, provided a 4 dB greater peak enhancement (23.2±1.2 dB) over the other concentrations (FIG. 17). The half-life at 37° C. of all glucose lyoprotected agents, however, remained constant at an average of 2.8±0.1 minutes, signifying that the concentration of glucose did not significantly affect the stability of ST68 (FIG. 18). Yet, with 200 mM of glucose, the final product (cake) after freeze-drying had evidence of collapse, melt back (thawing during drying), and crystallization. This caused reconstitution difficulties.

Experimental Example 9

Shelf-Life Study

Figure 19:
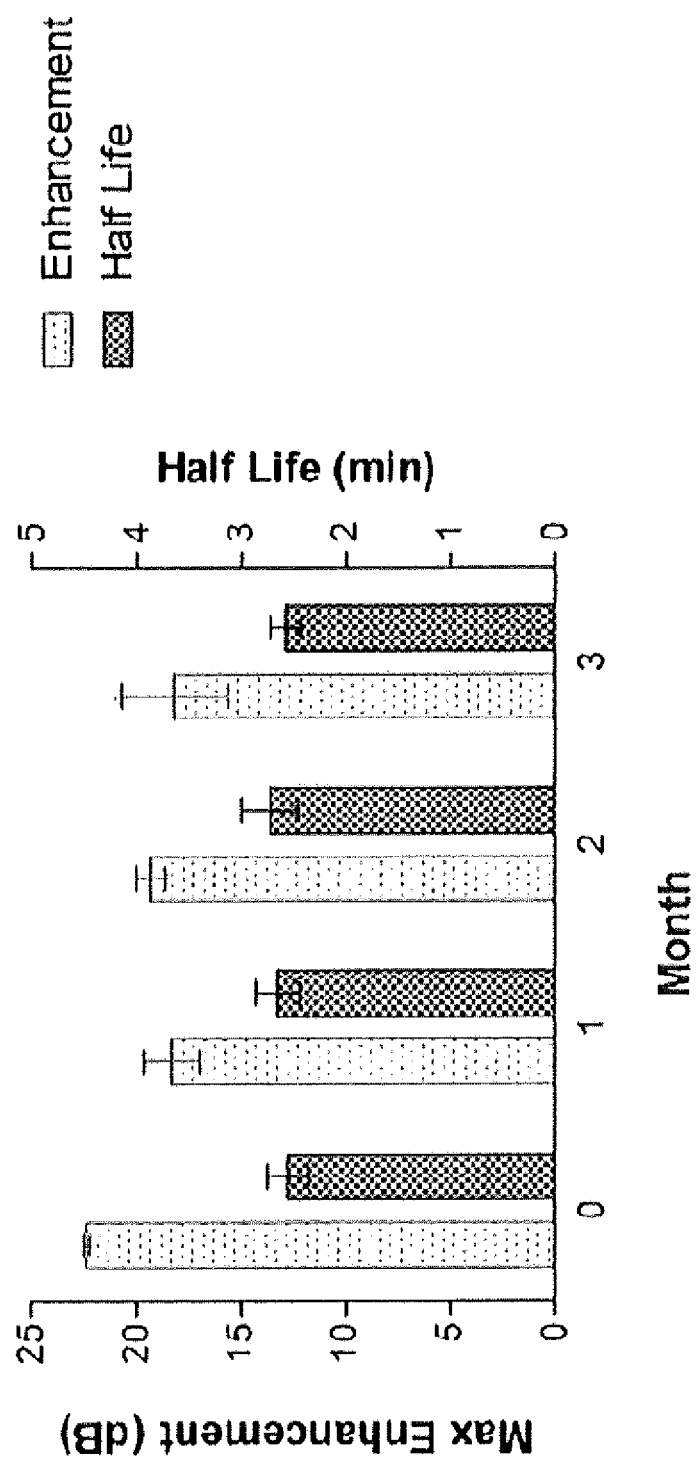
FIG. 19 depicts a bar graph of maximum echogenicity and half-life data of ST68G-100 tested over a period of 3 months at the start of each month. No statistical differences were measured (p>0.05). (f=5 MHz, 684 kPa, PRF=100 Hz).

ST68G-100 was tested at 100 µl/l for stability at the start of each month over a period of 3 months. No statistical differences were found (p>0.05), having an average maximum enhancement of 19.6±1.0 dB and a half-life of 2.6±0.1 minutes for the duration (FIG. 19). Originally, ST68 would be stable for a maximum of a few weeks, being stored at 4° C., before the collapse and coalescence of bubbles decreased the effect of the agent. Having a freeze-dried form of this agent stable for over 3 months at room temperature negates the need for immediate production prior to use.

Experimental Example 10

Scanning Electron Microscope Imaging

Figures 20A, 20B:
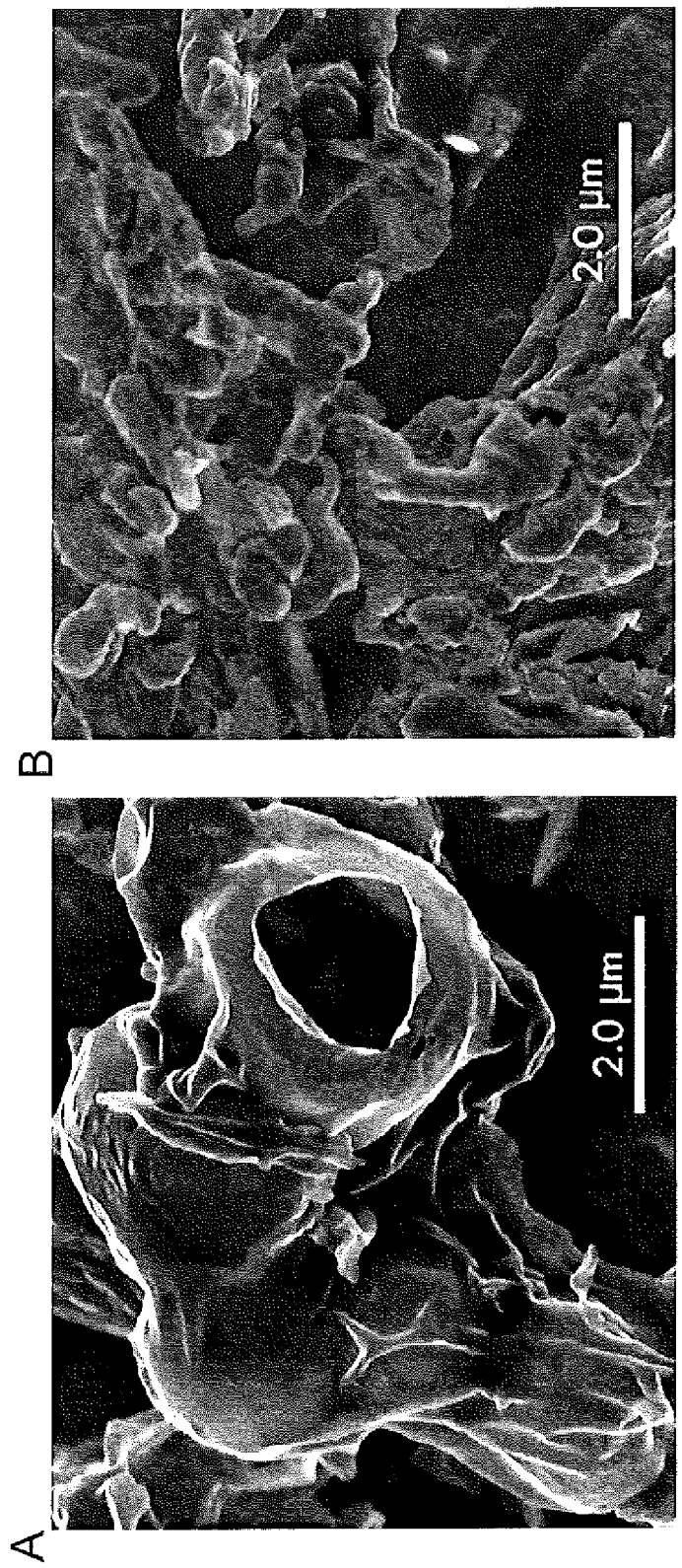
FIG. 20, consisting of panels A and B are a series of ZEISS® SUPRA™50 S.E.M. images of ST68G-100 (FIG. 20, panel A) and ST68 without lyoprotectant (FIG. 20, panel B) taken at 6,000× with an OXFORD ENERGY DISPERSIVE MICROANALYSIS™ (EDS) set to 3.5 kV and an aperture of 4 mm. (Size bar=2 μm).
Figure 21:
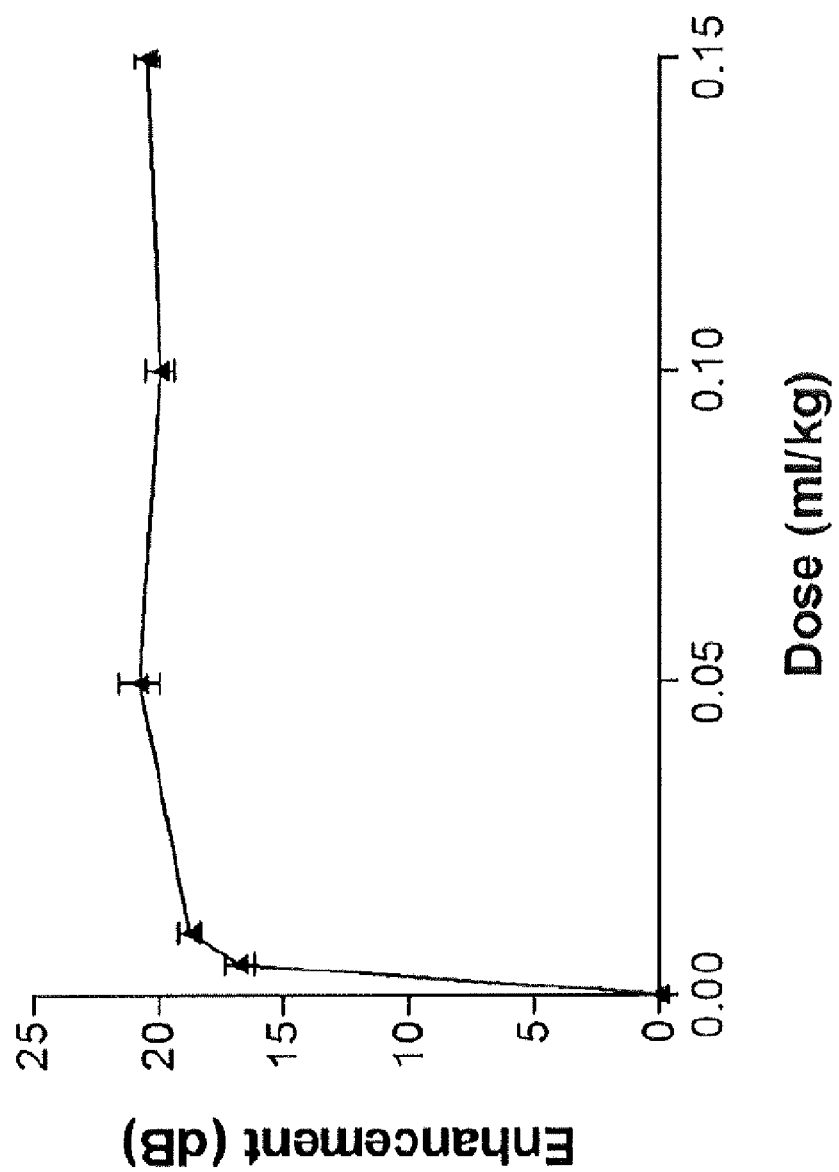
FIG. 21 depicts a dose response curves of ST68G-100 in-vivo performed on a New Zealand white rabbit with a SONIX® RP scanner on pulse Doppler mode at 5 MHz and a PRF of 6.7 kHz.
Figures 22A, 22B:
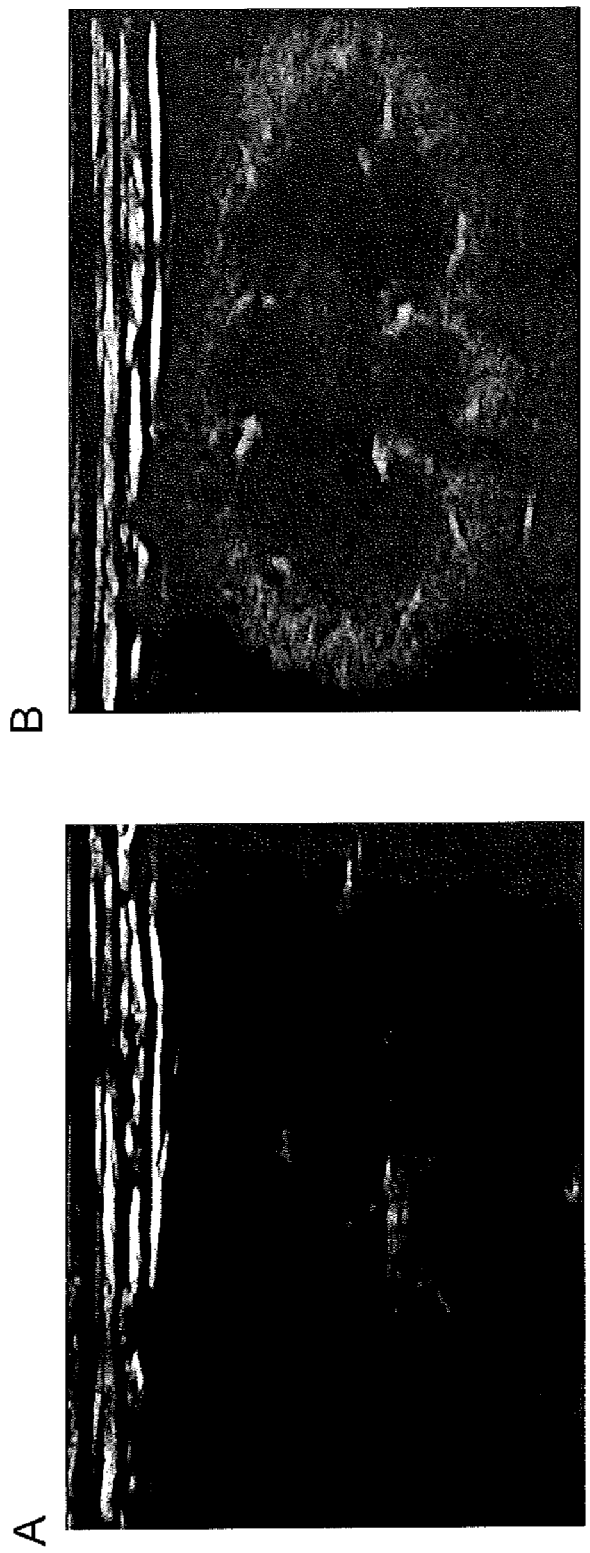
FIGS. 22A and 22B are a series of images of before (FIG. 22A) and 5 seconds after (FIG. 22B) 0.1 ml/kg injection of ST68G-100 into a 3.3 kg New Zealand white rabbit with enhancement lasting for at least 40 seconds (SONIX® RP scanner in pulse inversion mode at 5 MHz, PRF of 1 kHz, −8 power).

To show the difference between ST68G-100 and ST68 control (without lyoprotectant), S.E.M. images were taken of both samples after freeze-drying and PFC gas introduction. Protected bubbles can be seen in FIG. 20A while, without the addition of a lyoprotectant, bubbles are not present (FIG. 20B). The ruptured capsule in FIG. 20A clearly shows the hollow nature of these particles, as well as their fragile nature, since it could have been ruptured during sample preparation for imaging.

Experimental Example 11

In Vivo Study

Figure 11:
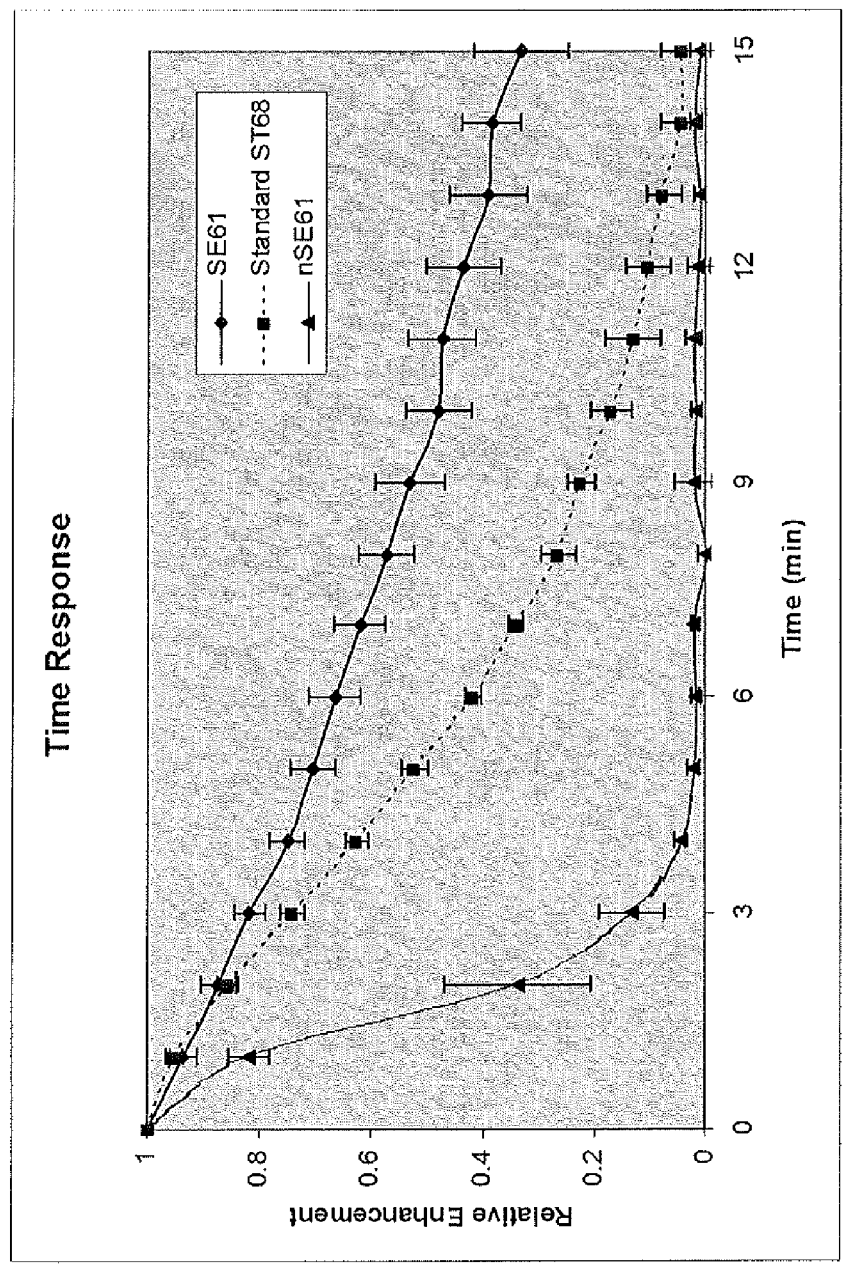
FIG. 11 is a graph depicting the time response curve for SE61 (solid diamonds), nSE61 (solid triangles) and standard ST68 (solid squares).

The in vivo dose response experiments of ST68G-100 (FIG. 10) were modeled after previous studies (Forsberg et al., 1996, supra; Wheatley et al., 2006, supra) of ST68 for direct comparison. Previously, a maximum peak enhancement of 26.1±0.5 dB (Forsberg et al., 1996, supra) and 23.7±2.9 dB (Wheatley et al., 2006, supra) were recorded for the native and nano ST68, respectively. The lyophilized agent, ST68G-100, was chosen for this study based on results outlined above and provided a peak enhancement of 20.8±0.8 dB, being 4 dB below the recorded average of native and nano ST68. A PIHI (5 MHz) of a New Zealand white rabbit kidney pre- and post-injection of a reconstituted freeze-dried ST68G-100 sample is depicted in FIG. 11. The vasculature and parenchyma boundaries of the kidney are clearly visible after injection of 0.1 ml/kg contrast. Additionally, pulse Doppler images (results not shown) of the same agent and injection volume were comparable to non-freeze dried examples.

These data demonstrate that surfactant-stabilized gas bubbles, such as ST68, can be freeze-dried, stored at about 4° for extended periods of time, and reconstituted, while successfully maintaining echogenicity both in vitro and in vivo and stability (e.g., half-life).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A freeze-dried ultrasound contrast agent (UCA) comprising:
   at least a first surfactant, wherein the first surfactant is a sorbitan monostearate;
   a second surfactant, wherein the second surfactant is a polyoxyethylene sorbitan monooleate; and
   a saccharide, wherein the saccharide is selected from the group consisting of glucose and trehalose.

2. A reconstituted UCA, comprising:
   a freeze-dried UCA and an excipient,
   wherein the freeze-dried UCA comprises:
      at least a first surfactant, wherein the first surfactant is a sorbitan monostearate;
      a second surfactant, wherein the second surfactant is a polyoxyethylene sorbitan monooleate; and
      a saccharide selected from the group consisting of glucose and trehalose.

3. The UCA of claim 1, wherein the UCA is a particle-stabilized UCA.

4. A method of making a lyoprotected ultrasound contrast agent (UCA), said method comprising the steps of:
   a) preparing a UCA comprising at least a first surfactant and a second surfactant, wherein:
      the first surfactant is a sorbitan monostearate; and
      the second surfactant is a polyoxyethylene sorbitan monooleate; and
   b) adding a lyoprotectant to the UCA to prepare a lyoprotected UCA,
   wherein the lyoprotectant is a saccharide selected from the group consisting of glucose and trehalose.

5. The method of claim 4, further comprising the step of
   c) freeze-drying the lyoprotected UCA, thereby preparing a freeze-dried UCA.

6. The UCA of claim 2, wherein the UCA is a particle-stabilized UCA.

7. The UCA of claim 1, wherein the saccharide is glucose.

8. The UCA of claim 1, wherein the saccharide is trehalose.

9. The UCA of claim 2, wherein the saccharide is glucose.

10. The UCA of claim 2, wherein the saccharide is trehalose.

11. The method of claim 4, wherein the saccharide is glucose.

12. The method of claim 4, wherein the saccharide is trehalose.

* * * * *